US006337214B1

(12) United States Patent
Chen

(10) Patent No.: US 6,337,214 B1
(45) Date of Patent: *Jan. 8, 2002

(54) DETECTION OF DNA, RNA AND PROTEINS USING A TEST COLUMN WITH TWO SNARES

(75) Inventor: Hai Xing Chen, Toronto (CA)

(73) Assignee: ACGT Medico, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/326,297

(22) Filed: Jun. 4, 1999

Related U.S. Application Data

(63) Continuation-in-part of application No. 09/093,532, filed on Jun. 8, 1998, now Pat. No. 6,174,733.

(30) Foreign Application Priority Data

Jun. 9, 1997 (GB) .............................. 9711941

(51) Int. Cl.$^7$ .................. G01N 33/566; G01N 33/558; C12Q 1/68; C07H 21/02; B01D 15/00
(52) U.S. Cl. .................. 436/501; 436/513; 436/514; 436/518; 435/6; 435/7.1; 435/91.1; 435/91.2; 435/283.1; 435/285.1; 536/23.1; 536/24.3; 536/24.31; 536/24.32; 536/24.33; 210/656; 210/635; 210/348; 210/500.26
(58) Field of Search ............................. 435/4, 5, 6, 7.1, 435/91.1, 91.2, 283.1, 285.1, 286.5; 536/23.1, 24.3, 24.31, 24.32, 24.33; 436/501, 513, 514, 518; 210/656, 635, 348, 500.26

(56) References Cited

U.S. PATENT DOCUMENTS 4,832,916 A * 5/1989 Gilak .................. 422/70
5,642,816 A * 7/1997 Kelly et al. .................. 211/60.1
5,804,384 A  9/1998 Muller et al.
5,876,918 A * 3/1999 Wainwright et al. ............ 435/4

FOREIGN PATENT DOCUMENTS

| EP | 0 387 696 A3 | 8/1990 |
| EP | 0 605 828 A1 | 7/1994 |
| EP | 0 780 479 A2 | 6/1997 |
| EP | 0 846 776 A2 | 10/1998 |
| GB | 2 283 569 A | 10/1995 |
| GB | 2 324 370 A | 10/1998 |

OTHER PUBLICATIONS

Sambrook et al Molecular Cloning A Laboratory Manual pp.s 5.78–5.79 1989.

* cited by examiner

Primary Examiner—Kenneth R. Horlick
Assistant Examiner—Jeffrey Siew
(74) Attorney, Agent, or Firm—Yi Li

(57) ABSTRACT

Methods and apparatuses are disclosed for detecting the presence of a test material in a test sample. The test sample is introduced into a test column which has at least two snares. One of the snares has a control capture material for detection of the presence of control. Each of other snares has a capture material specific to a corresponding test material for which detection being sought. The capture material will bind with the corresponding test material to form a bound material. The test column is then washed to remove materials which have not been bound to the capture materials. Finally, the presence of bound materials is detected on each of the snares. The method is useful for detection of a pathogen indicator in a test sample, particularly suitable for detection of DNA and RNA.

43 Claims, 11 Drawing Sheets

DETECTION OF DNA, RNA AND PROTEINS USING A TEST COLUMN WITH TWO SNARES

This application is a continuation-in-part of patent application Ser. No. 09/093,532, filed Jun. 8, 1998, now issued as U.S. Pat. No. 6,174,733 issued on Jan. 16, 2001.

FIELD OF THE INVENTION

The present invention relates to an apparatus and method for the detection of test materials in small concentrations, especially the detection of pathogen indicators. In particular it relates to the detection of DNA, RNA and proteins in serum.

BACKGROUND TO THE INVENTION

Historically, the diagnosis of diseases has depended upon clinical manifestations. However, new techniques of detecting diseases have been developed with the advent of nucleic acid and monoclonal antibody detection methods. The detection of nucleic acid has been used for diseases associated with abnormal gene products, such as anemia, Huntington's disease and certain thalassemia mutations. In addition, the detection of nucleic acid has been used for bacterial and viral diseases, such as Human Immunodeficiency Virus (HIV). Moreover, monoclonal antibody detection methods have gained acceptance for the identification and differentiating of certain diseases such as cancers.

As appreciated by those skilled in the art, the detection of a pathogen indicator has applicability to the detection of certain diseases associated with abnormal genes, certain diseases associated with the presence of an identifiable nucleic acid sequence and certain diseases associated with the immune system. The pathogen indicator described herein includes DNA, RNA, antibody, antigen, and other proteins.

Known manual pathogen indicator detection methods in research and clinical laboratories tend to have low accuracy, low sensitivity and are subject to human error, both in carrying out the methods and in interpreting the results. Other methods, e.g. culturing methods, are not suitable for many diseases. For example, tuberculosis has a very slow growth rate, which makes detection not easy or even not possible.

U.S. Pat. No. 5,753,439 to Smith et. al. describes a method to detect characteristic dinucleotide and trinucleotide acid sequences, to determine target sequences and to screen for genetic defects and disorders associated with the sequences. The assays are conducted on solid surfaces allowing for multiple reactions to be conducted. However, the method does not provide a control process to provide assurances that the results are accurate and sensitive to determining if there is an error in the method.

U.S. Pat. No. 5,824,478 to Muller describes a method wherein a sample is contacted with a detector probe and a capture probe to form a detector probe-analyte-capture probe complex which is used to detect a target analyte in a sample. The target analytes, capture probes, and detector probes can be nucleic acids and polypeptides. However, the method does not provide a control process to provide assurances that the results are accurate and sensitive to determining if there is an error in the method.

In a standard enzyme ELISA method for immunoassay, a tray with a plurality of wells, e.g. 96 wells, containing appropriate antibodies is used. One method to eliminate error in this ELISA is to use a control. One of the wells can be used as a positive control (with a positive antigen), while the remaining wells can be used for testing patient's sera. After addition of the serum samples, the wells are washed and a second antibody, which carries an enzyme, is added to the wells. After washing again, a substrate is added. The substrate and enzyme react, with a color reaction. The color yield from the reaction is associated with the presence of an antigen. The method is rife with possibilities for error. Human error can lead to some wells being washed twice or not at all, having reagents added twice or not at all, or wells being inadvertently contaminated with extraneous materials. For example, over washing tends to flush all the components and create a false negative result, while an incomplete wash will provide detection from non-binding materials and yield false positive results. The control well can give no assurance that the results from any other well is indicative of the presence or otherwise of the pathogen indicator under investigation. Additionally, color differences from well to well give additional uncertainties with respect to interpretation of the results.

Most of the previous tests are demanding of time, skill and concentration. So much so, that in many jurisdictions the number of tests that can be conducted by one technician is limited by regulation. This serves to raise the cost of testing, as it is so labour dependent.

For all the above reasons, and more, a new method, apparatus and a kit for detecting a pathogen indicator is desirable, which is accurate, reproducible, and is sensitive to determining if there is an error in the method.

SUMMARY OF THE INVENTION

The present invention provides a method for detecting the presence of a test material in a test sample. The method comprises the steps of: (a) introducing a test sample and a control material into a test column, wherein the column has at least two snares, one of said snares having a control capture material; at least one of said snares thereon having a target capture material specific to a corresponding test material in the test sample for which the detection is being sought, so that the control capture material will bind with the control material to form a bound control material; and the target capture material will bind with the corresponding test material to form a bound material; (b) washing the test column to remove any materials which have not been bound to the capture materials; and (c) detecting the presence of bound materials on each of the snares. The method can further comprise adding a label material for each of the bound materials to form labeled bound materials and then detecting the presence of the labeled bound materials.

In another embodiment, the present invention provides a method for detecting the presence of a DNA sequence in a test sample. The method comprises the steps of: (a) denaturing a test sample to form a single strand target DNA sequence for which detection is being sought; (b) introducing the test sample and a first control single strand DNA sequence into a test column which has at least two snares, one of said snares having a first control single strand capture DNA sequence; at least one of said snares thereon having a target single strand capture DNA sequence specific to the corresponding target DNA sequence in the test sample; and wherein the target single strand capture DNA sequence will bind with the corresponding target DNA sequence in the test sample to form a double strand DNA sequence, and the first control single strand capture DNA sequence will bind with the first control DNA sequence to form a double strand control DNA sequence; (c) adding a wash solution to the column to remove unbound DNA; (d) adding an enzyme to the column to destroy single strand DNA; (e) adding a denaturing solution to separate the formed double strand DNA sequences, then adding a wash solution to remove denatured non-capture single strand sequences, so that the single strand capture DNA sequences re-form on each snare; (f) adding DNA probes to provide detectable labels for single strand capture DNA sequences formed in step (e); (g) adding a wash solution to the column to remove unbound DNA probes; and (h) detecting any signals from each snare. In step (b), the first single strand control DNA sequence can be added into said test sample prior to introducing the sample into the test column, or can be added into the test column separately from the test sample. Moreover, the method can further include adding a substrate which reacts with the labels to give off detectable signals.

Additionally, the method further comprises introducing a second control single strand DNA sequence into the test column; wherein the test column has a control snare thereon having a second control single strand capture DNA sequence.

In a further embodiment, the snares have more than one single strand capture DNA sequences on one single snare, and the labels are different for different single strand capture DNA sequences on one single snare so that different DNA sequences can be detected on one single snare.

In yet another embodiment, the method for detecting the presence of a DNA sequence in a test sample comprises the steps of: (a) providing a positive control single strand DNA sequence; (b) denaturing a test sample to form a single strand target DNA sequence for which detection is being sought; (c) adding the test sample and the positive control DNA sequence to a test column, wherein the column has at least two snares, one of said snares having thereon a first control single strand capture DNA sequence for binding to a portion of the positive control DNA sequence; at least one of said snares thereon having a target single strand capture DNA sequence specific to the corresponding target DNA sequence in the test sample, so that the positive control DNA sequence binds with the first control single strand capture DNA sequence wherein the bound positive control DNA sequence has a double strand portion and a single strand portion; and the target DNA sequence present in the test sample binds with the target single strand capture DNA sequence wherein the bound target DNA sequence has a double strand portion and a single strand portion; (d) adding a wash solution to the column to remove unbound DNA; (e) adding DNA probes to provide detectable labels for attachment to the single strand portion of the bound positive control DNA sequence and the single strand portion of the bound target DNA sequence formed in step (c); (f) adding a wash solution to the column to remove unbound DNA probes; and (g) detecting any signals each snare. In addition, the method can further include adding a substrate which reacts with the labels to give off detectable signals.

The positive control single strand DNA sequence is prepared from a target DNA sequence for which detection is being sought, by a process selected from the group consisting of (1) inserting a control DNA fragment into the target DNA sequence for which detection is being sought at a predetermined scission point; and (2) removing a small fragment of DNA from the target DNA sequence at a predetermined scission point.

Further more, step (c) of the method can further include adding a negative control DNA sequence to the test column; wherein the test column also has a control snare having thereon a second control single strand capture DNA sequence for binding to the negative control DNA sequence, so that the negative control DNA sequence binds with the second control single strand capture sequence to form a bound negative control DNA sequence. The negative control single strand DNA sequence is different from the target DNA sequence and different from the positive control DNA sequence.

In a further aspect, the present invention provides a method for detecting the presence of a RNA sequence in a test sample. A method for detecting the presence of a RNA sequence in a test sample comprises the steps of: (a) providing a positive control single strand DNA sequence; (b) adding a test sample and the positive control DNA sequence to a test column wherein the column has at least two snares, one of said snares having thereon a first control single strand capture DNA sequence for binding to the positive control DNA sequence; at least one of said snares thereon having a target single strand capture DNA sequence specific to the corresponding target RNA sequence in the test sample, so that the positive control DNA sequence binds with the first control capture DNA sequence to form a double strand positive control DNA sequence, and the RNA sequence present in the test sample binds with the target capture DNA sequence to form a double strand DNA/RNA complex; (c) adding a wash solution to the column to remove unbound positive control DNA and target RNA; (d) adding an enzyme to the column to destroy single strand DNA and RNA; (e) adding a denaturing solution to separate the formed double strand control DNA sequence and double strand DNA/RNA complex, then adding a wash solution to remove denatured non-capture single strand DNA and RNA sequences, so that the single strand capture DNA sequences re-form on each snare; (f) adding DNA probes to provide detectable labels for single strand capture DNA sequences formed in step (e); (g) adding a wash solution to the column to remove unbound DNA probe; and (h) detecting any signals from each snare. In addition, the method can further include adding a substrate which reacts with the labels to give off detectable signals.

In one embodiment, the positive control single strand DNA sequence is different from the target RNA sequence and the first control single strand capture DNA sequence is different from the target single strand capture DNA sequence. In addition, the DNA probes used in step (f) are different for the first control capture and the target capture sequences.

In another embodiment, the positive control single strand DNA sequence has a portion which has the same sequence to a portion of the target RNA sequence. The first control single strand capture DNA and the target single strand capture DNA have a common sequence at a portion of the capture sequences, so that a common DNA probe is used in step (f) for detection of the re-formed control and target capture sequences.

In a further embodiment, step (a) of the RNA detection method further includes providing a negative control single strand DNA sequence which is different from the target RNA sequence and different from the positive control DNA sequence. Step (b) further includes adding the negative control DNA to the test column which also has a control snare having thereon a second control single strand capture DNA sequence. The second control capture DNA sequence partially matches the negative control DNA sequence so that the negative control DNA sequence binds with the second control capture DNA sequence to form a double strand DNA sequence which also has unbound single strand portions. Step (f) DNA probes do not match re-formed partial second control single strand capture DNA sequence formed in step (e), and no binding occurs between them. Therefore, in step (h) no signal is detected from the second control snare under normal conditions.

In yet another embodiment, the second control single strand capture DNA sequence is different from the target capture DNA and the first control capture DNA sequences.

In an additional embodiment, the first control capture DNA, the second control capture DNA and the target capture DNA have a common sequence at a portion of the capture sequences. A common DNA probe is used in step (f) for detection of the re-formed control and target capture sequences.

In another aspect, the present invention provides a column for analysis of a test material, wherein the column has at least two snares, one of said snares having thereon a first control capture material for detecting the presence of a first control material, and at least one of said snares having thereon a test capture material for detecting a test material for which detection is being sought. The column can also comprise at least two chambers, each chamber having a snare, one of said chambers having a first control capture material on the snare for detecting the presence of a first control material, and at least one of said chambers having a test capture material on the snare for detecting the test material for which detection is being sought.

In a further embodiment, the chambers have a connecting means to connect different chambers in order, and the chambers are connected along the longitudinal axis of the chamber through the connecting means. Alternatively, the chambers can be placed side-by-side. Furthermore, the snares can reside on a snare tray which is in a plane transverse to a longitudinal stem. When the stem rotates, the snares will be conveyed to the sample station, reagent stations, and detection stations.

Additionally, the column further has a chamber or a snare having a second control material on the snare for detecting the presence of a second control material.

In a further aspect, the present invention provides a kit. The kit comprises (a) a column for analysis of a test material, wherein the column has at least two snares, one of said snares having thereon a first control capture material for detecting the presence of a first control material, and at least one of said snares having thereon a capture material for detecting a test material for which detection is being sought; (b) reagents for detecting the presence of the test materials.

In an additional aspect, the present invention provides an apparatus for detection of a test material in a sample. The apparatus comprises (a) a column handler system which comprises column holders and an column off-loader which unloads a test column; (b) a sample station for adding a sample to a test column; (c) a reagent station; (d) a detection station for detection of a control material and the test material in the testing column; and (e) a carousel comprising a rotating frame which carries the column holder; wherein the carousel conveys the test column to the sample station, reagent station, and detection station.

In another embodiment, the detection station has a plurality of detectors for detecting the presence of one or more control materials and one or more test materials on the snares.

In an additional aspect, the present invention provides a sample dispenser comprising: (a) a sample holder which comprises a side wall, and a bottom connected to the side wall; wherein said bottom has a bore which is sealed with a film capable of being punctured; and (b) a puncturer thereon having a delivering spout for puncturing said film of the bore.

The puncturer of the sample dispenser connects to a test column. When the sample holder is situated on top of the puncturer and lowered toward the column, the puncturer punctures the film of the sample holder to dispense a liquid sample in the sample holder into the test column.

DETAILED DESCRIPTION OF PREFERRED EMBODIMENTS

In one aspect, the present invention provides an apparatus for detection of a test material in a sample. The apparatus comprises:

(a) a sample addition station for adding a sample to a test column having at least two snares;

(b) at least one reagent station, and one washing station;

(c) a detection station for detection of the control material and the test material in the test column; and (d) conveying means for conveying the test column from the sample addition station to the reagent station, the washing station, and the detection station.

The test column is loaded into the apparatus either automatically or manually. The test column can have different shape and configurations. In general, the column has at least two snares, one of the snares having thereon a first control capture material for detecting the presence of a first control material, and the other snare having thereon a capture material for detecting a test material for which detection is being sought. The column can also have at least two chambers, each chamber having a snare, one of the chambers having a first control capture material on the snare for detecting the presence of a first control material, and the other chamber having a capture material on the snare for detecting a test material for which detection is being sought. Detail descriptions and examples of the test columns are given hereinafter.

Each reagent station has delivery means for delivering a measured quantity of reagent to the column, and each washing station also has delivery means for delivering a measured quantity of washing solution to the column. The detection station has one or more detectors for detecting the signals from the testing column.

Optionally, the apparatus can further comprise additional stations for recycling used test columns. The additional stations include:

(a) a stripping station for adding a stripping material to the test column, in order to strip the test material from the capture material;

(b) a first washing station after each stripping station, for adding a wash material in order to wash stripped test material from the column;

(c) a first detection station for detecting the presence of the test material; and (d) conveying means for conveying test columns to each of the stripping station, washing station and detection station.

The apparatus can also have a second stripping station, second washing station and second detection station for further stripping, washing and detection to complete the recycling process.

Figure 1:
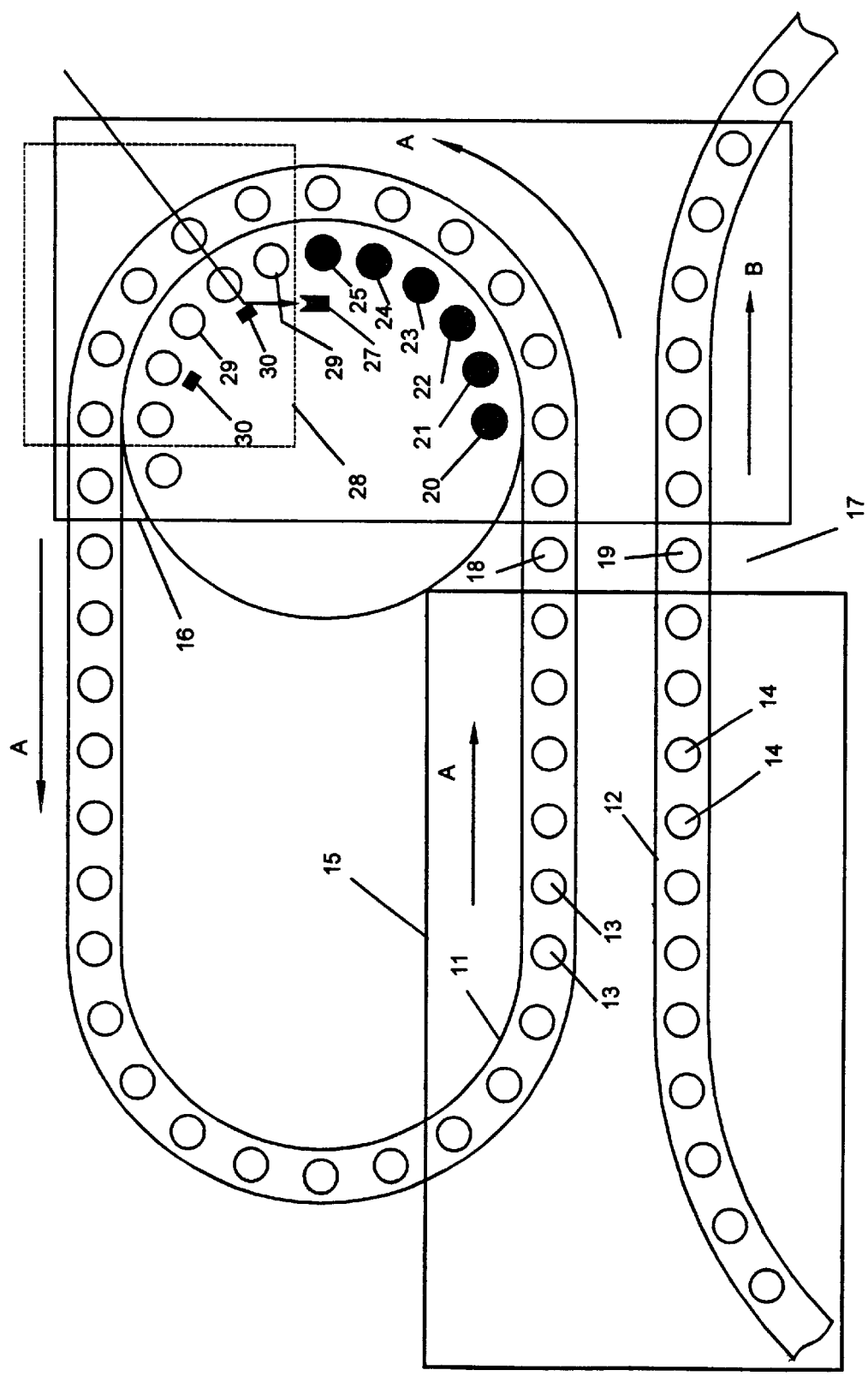
FIG. 1 is a partial general layout of an apparatus for carrying out one embodiment of the present invention.

In one embodiment, an apparatus is illustrated in FIG. 1. The apparatus comprises a column conveyor 11 and a test tube conveyor 12, each of which has means (not shown) associated therewith for moving the conveyors, generally in the directions shown by arrows A and B. Column conveyor 11 has a plurality of columns 13 which are equidistantly attached to column conveyor 11. Attachment of columns 13 to column conveyor 11 is preferably temporary so that used or defective columns can be removed and replaced. Test tube conveyor 12 has a plurality of test tubes 14, e.g. serum tubes. Preferably the test tubes 14 are equidistantly attached to test tube conveyor 12. Attachment of the test tubes 14 to the test tube conveyor 12 is preferably temporary so that used or defective test tubes can be removed and replaced. The means for moving the conveyors are preferably indexing means (not shown). The conveyors 11 and 12, test tubes 14 and columns 13 are covered within housings 15 and 16, apart from a window 17 which is wide enough to accommodate only one column 18 and an associated test tube 19. The column conveyor 11 and the test tube conveyor 12 are indexed so that only one test tube 19 is adjacent to an associated column 18, when in window 17.

Within housing 16, there are a number of reagent stations, for example reagent stations 20–25, for adding reagents to the columns as the columns index past the stations. When a reagent station adds a washing solution to the columns, the reagent station is also called a washing station. At the end of the reagent stations or downstream thereof, there is detector means 27. In the embodiment shown in FIG. 1, there is also a cleaning zone 28. In the cleaning zone there is a series of wash stations 29, possibly stripping stations for stripping unwanted materials from the column, and associated detectors 30.

It will be understood that instead of a series of wash stations, stripping stations and detector stations, there may be a single wash station, stripping station and detector station and a column is caused to pass the wash station, stripping station and detector station again if any contamination is detected on the first pass of the column past the detector station. This can be accomplished with a rotating table, for example.

Figure 12:
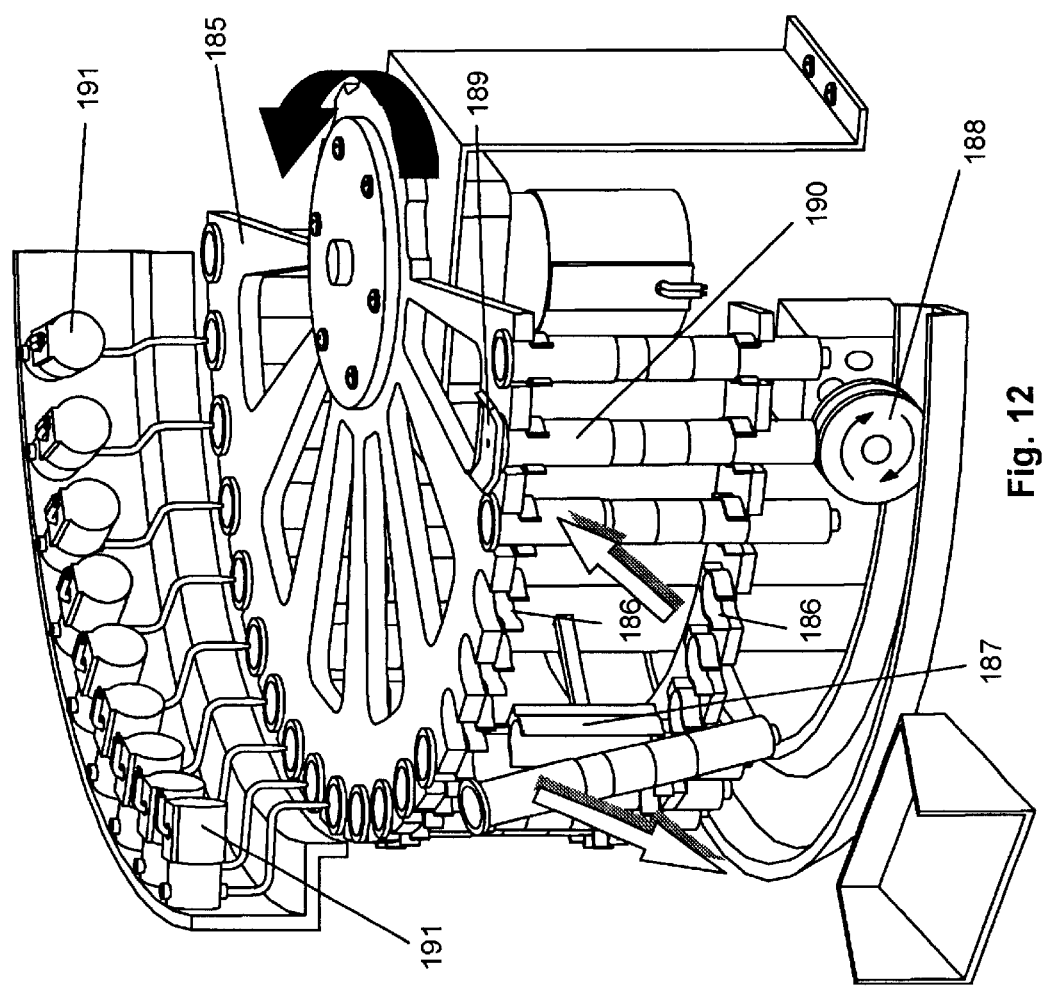
FIG. 12 shows a general view of another apparatus for carrying out one embodiment of the present invention.

Another type of apparatus is illustrated in FIG. 12. The apparatus has a column handler system which comprises column holders, 186, and an column off-loader, 187. The column off-loader unloads a test column after a sample analysis is complete or when a problem is detected with a test column. As illustrated, the apparatus has a carousel with a rotating frame, 185, which carries the column holders. The carousel conveys the test columns to the sample station, reagent station, and detection station during the sample analysis. The column handler system can further comprises an automated column loader.

Figure 10:
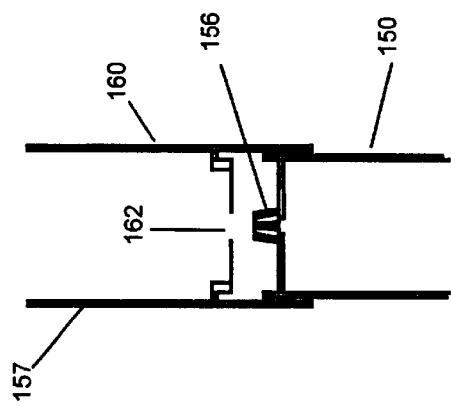
FIGS. 10A and 10B show a column and a sample dispenser prior to use, and in use, respectively.
FIG. 10C is a partial cross-sectional view of the column and sample holder of FIGS. 10A and 10B just prior to connection of the sample holder and the puncturer.
Figure 10:
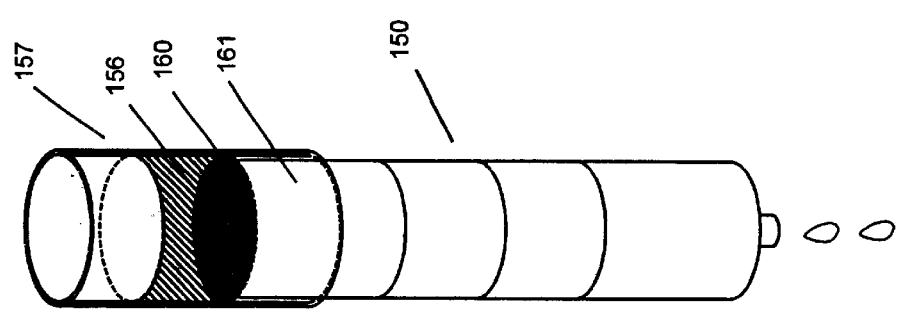
Figure 10:
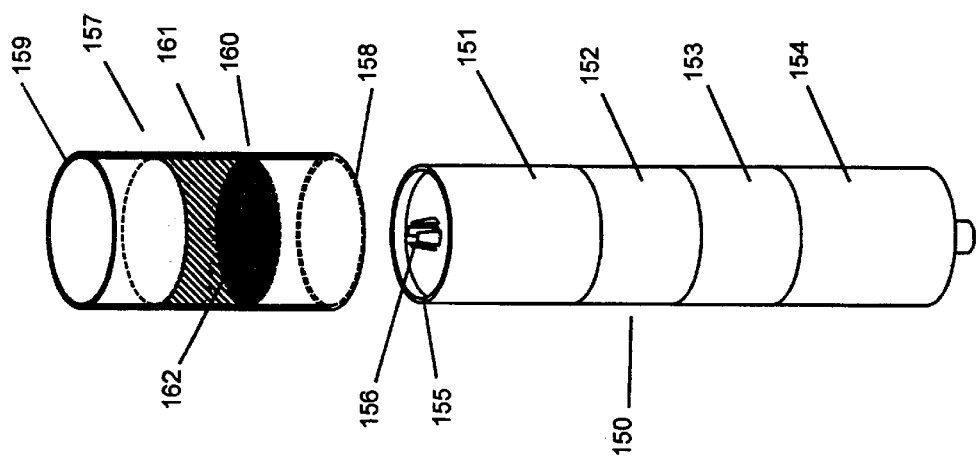

The apparatus has a sample station for adding a sample to a test column. The sample station comprises a column pusher, 188, and a pressure plate, 189, aligned on top of the column pusher. With a sample station shown in FIG. 12, a sample dispenser, 190, is used together with a test column for a detection process. The details of the sample dispenser are described hereinafter in FIG. 10. In general, a sample dispenser situated on top of a test column. Under a downward physical pressure, the sample dispenser will dispense a liquid sample into the test column. When a test column and a sample dispenser are loaded into a column holder of the carousel and when the carousel conveys the column to pass the sample station, the column slides up to the top of the column pusher while stays underneath the pressure plate. The pressure generated on the column causes the sample dispenser to dispense the liquid sample into the test column. The column pusher shown in the figure is circular with a center slot to fit column drain outlet. To operate, the pusher can either rotate, or in a stationary condition. Other shapes can also be used for the pusher, for instance, elliptical shape.

Alternatively, a sample can also be added into the test column by a syringe pump or manually. The apparatus also has reagent stations, 191, and detection stations (not shown) for detection of a control material and the test material in the testing column.

Figures 2A, 2B:
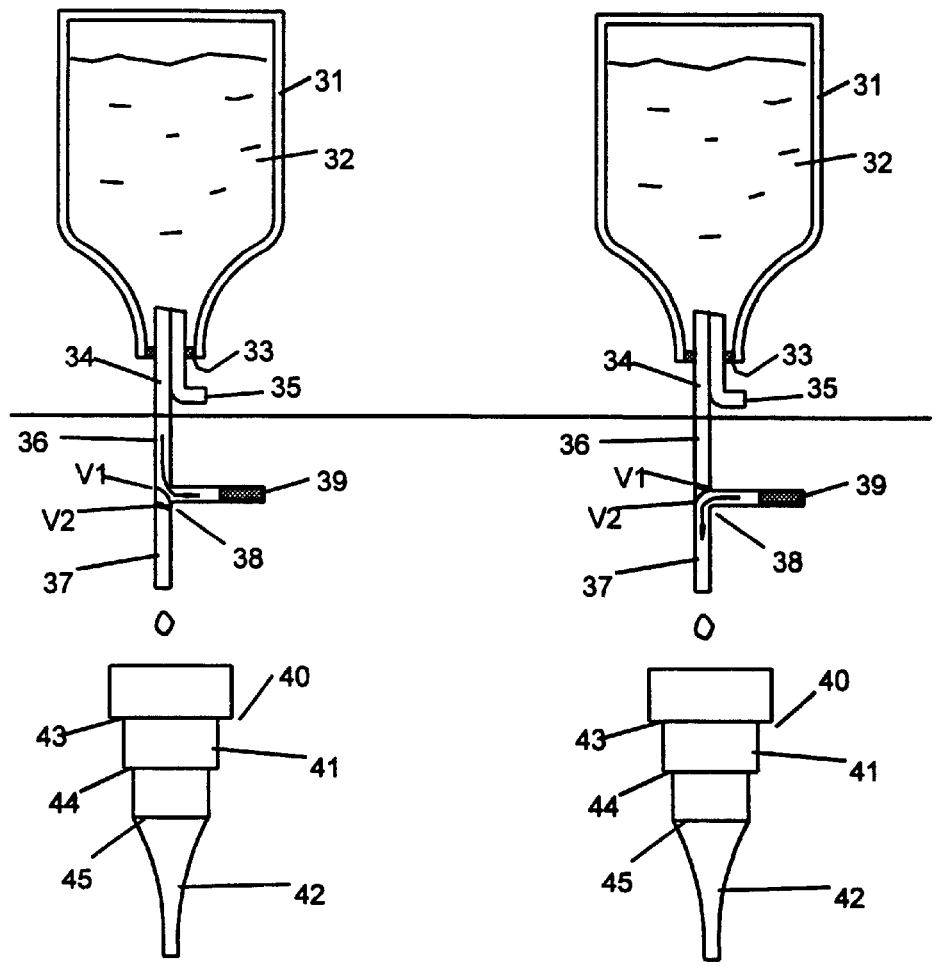
FIGS. 2A and 2B show a reagent delivery station for delivering a reagent to a column.

FIGS. 2A and 2B show one type of reagent station and one type of column. At the reagent station there is a reagent bottle 31 with reagent 32 therein. The reagent bottle 31 has a rubber septum 33 through which a double-hollow needle 34 may penetrate. The double-hollow needle 34 has one tube 35 which is connected to an air supply (not shown). A second tube 36 is connected to a delivery tube 37 by a double valve junction 38. Also connected to double valve junction 38 is a measuring syringe 39. Second tube 36 and delivery tube 37 may be a single tube with a double valve junction therein. Valves V1 and V2 in double valve junction 38 allow reagent 32 to be drawn into measuring syringe 39 and then be expelled from measuring syringe 39 through delivery tube 37. Column 40 is situated just below delivery tube 37 so that reagent may be transferred, e.g. by gravity, to column 40. Alternatively there may be a liquid-tight connection between delivery tube 37 and column 40. The reagents may be urged through the columns by means of pressure from the top or vacuum attached to the discharge tube.

In another aspect, the present invention also provides a column for analysis of a test material in a sample. The test material herein includes, but not limited to, DNA, RNA, PNA, antibody, antigen, protein and a material that specifically binds to DNA, RNA and proteins. Preferably, the test material is a pathogen indicator, such as DNA, RNA and antigen. The column has at least two snares, one of said snares having thereon a first control capture material for detecting the presence of a first control material, and the other of said snares having thereon a test capture material for detecting a test material for which detection is being sought. The column can also have at least two chambers, at least one of the chambers containing a snare thereon having a first control capture material, and at least one of the chambers containing a snare thereon having a test capture material for detecting a test material for which detection is being sought. Each chamber has a connecting means to connect the chambers in order. Furthermore, the chambers can also be placed side-by-side.

The term of test material used here means the material in a test sample for which detection is being sought. It is also referred to as target material, target protein, target DNA, target RNA, target antigen depending on the specific application. The term of test capture material means the capture material that specifically binds with a test material for which detection is being sought. The test capture material is also referred to as target capture material, target capture protein and target capture DNA depending on its specific application.

In addition to a snare having thereon a first control material, a column can have a plurality of snares each having thereon a different capture material for detecting more than one test material in a test sample. Optionally, a column can further have a snare having thereon a second control capture material for detecting the presence of a second control material. Moreover, a column can have an additional chamber with a snare without a capture material thereon. This snare can be used for detecting background signals of the detection method.

The capture materials for detecting the control materials and the test material for which detection is being sought include, but not limited to, single strand DNA sequence, antibody, antigen and protein. The selection of appropriate capture material depends on the specific detection being sought.

Alternatively, a snare tray can also be used for the method of detection. The snare tray has a plurality of snare locations in a plane transverse to a longitudinal stem. A detection station has a plurality of detectors which can be used for detecting the presence of control or test materials at the snare locations.

Figure 3:
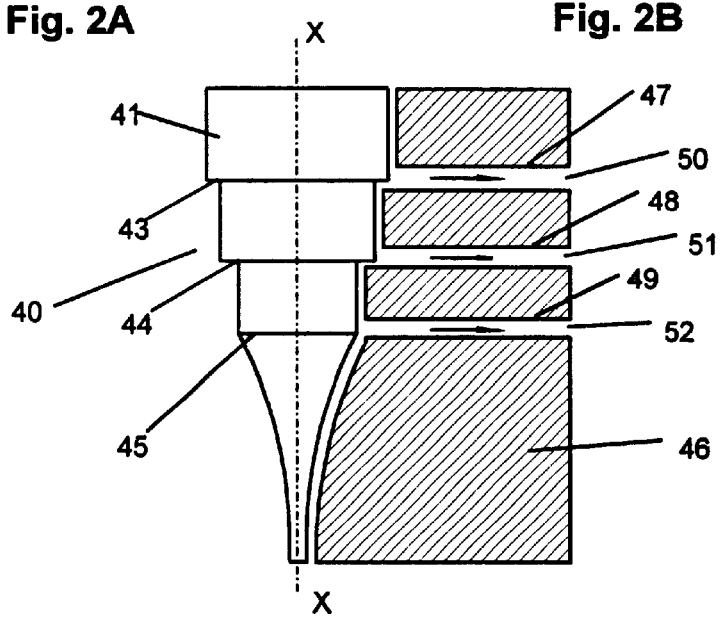
FIG. 3 shows a detector for detecting a signal from a column.

FIG. 3 shows one type of column. Column 40 comprises a column casing 41 and a discharge tube 42, Column casing 41 houses three snares 43, 44 and 45, which are spaced apart from one another by an intervening air space. The snares are spaced apart along longitudinal axis X—X of column 40. Although three snares are shown in FIGS. 2A and 2B, there should be at least two snares in a column. At least one of the snares is used for detecting a control material, and at least one of the snares is used for detecting the presence or otherwise of a material in a test sample. Snares 43–45 may be made from any suitable material for attaching a capture material as will be explained in more detail hereinafter, Typically the snares are made from a material with high surface area, e.g. sintered glass, sintered plastic, glass fibre, beads, chips, granules, and membrane. When membrane is used, a solid support may be required. One example of a snare is a layer of fine latex particles thereon having capture antibodies attached covalently, wherein the latex particles spread out on a porous sintered glass plate. The snares may sometimes be referred herein as glass frits or a fibre chips. The column casing adjacent to the snares are preferably light transparent, for better detection of chemiluminescent or other chemical reaction.

It is preferable that the snares be in a particular order, so that there may be positive identification of any reaction at a particular snare position. Clearly, it is important that detection of any reaction be identified with a particular capture material. For example, it is important that detection of any reaction with a control capture material, e.g. albumin, be positively identified with that control capture material and not with any other capture material, e.g. tuberculosis capture material. For this reason it is preferable that there is means to ensure that the order of the snares and their associated capture materials follows a predetermined order.

The column 40 may take any convenient shape, cylindrical, square, rectangular, or cylindrical with one flat side. In the FIGS. 2A, 2B, 3, 5A to 5C, column 40 is a step-shaped tube. Such a shape makes it necessary to make snares 43, 44 and 45 to be of different diameters. As will be described in more detail hereinafter, each of the snares may have a different capture material attached thereto. As described in general above, it may be important that a snare with a first capture material always be placed in the top position 43. Making snare 43 in a larger diameter than the other snares ensures that snare 43 cannot be placed in the position reserved for snare 44 or snare 45. Conversely, making a snare 45 in small diameter, with a different capture material to the capture material on snare 43, ensures that snare 45 cannot be placed in the position of snare 43 or 44. Obviously this is helpful in ensuring that the snares are correctly placed in the column. Of course, columns with correctly placed snares may be accomplished in other ways and so the stepped-tube arrangement shown in FIGS. 2A, 2B, 3, 5A to 5C is not essential. As will be apparent, the column may have a circular cross-section, a square cross-section or other suitable shape.

As will be described hereinafter at least one of the snares, e.g. 43 is used as a control. In some situations a second snare, e.g. 45 is also used as a second control, as will be described in reference to use of the columns and apparatus. The third snare, e.g. 44, is for testing for presence of a particular chemical from a sample in a test tube, e.g. a pathogen indicator in a patient's serum.

In FIG. 2A, the upper valve V1 of double-valve junction 38 is open and the lower valve V2 is closed, to allow a measured amount of reagent to be drawn into measuring syringe 39. In FIG. 2B, the upper valve V1 of double-valve junction 38 is closed and the lower valve V2 is open, to allow the measured amount of reagent in measuring syringe 39 to be expelled through delivery tube 37.

FIG. 3 shows column 40 adjacent to detector means. In the embodiment shown, in order to avoid false readings, detector block 46 is shaped to accommodate the shape of column casing 41. Detector block 46 has channels 47, 48, 49 for allowing any signals emanating from snares 43, 44, 45 to pass to detectors 50, 51 52, respectively. Another advantage of the stepped column casing as shown in FIG. 3 is that signals from each of the snares are prevented from filtering through to an adjacent detector channel. Although UV detectors may be used in certain instances, laser detectors are preferred.

Some reactions are chemiluminescent and detection of the chemiluminescence may be determined directly from light emanating from the snare, as implied from the positioning of channels 47–49 in FIG. 3. However, sometimes it may be necessary to measure the light emanating at an angle from the top surface of each snare. Accordingly, the channels would then be angled to guide such light to an appropriate detector.

Other reactions may require a different detection system. For example, it may be necessary to have a light source for detecting certain reactions, as will be understood by those skilled in the art. In addition, columns different from those of FIG. 2A may require different arrangements for the detection apparatus, as will be described hereinafter.

Although FIG. 3 shows a means, for example, for minimizing cross-over of light from snare 43 to channel 48, if reaction times are in the order of milliseconds and there is a substantial time interval between reactions from adjacent snares, it may not be as critical to prevent light cross-over from one detector to another.

Signals from the detectors may be displayed in a number of ways. For example, the signals may be displayed graphically on paper or on a monitor. The signals may also be manipulated to assess the concentration of pathogen indicators on the various snares. The data from the signals may be stored electronically and then retrieved either locally or remotely. In addition to the data, software can be used to provide information concerning the tests performed and thus enhance the viewer's understanding and interpretation of the results. One of the advantages of remote access to the results is that a doctor who requests the tests may review the raw data both rapidly and directly, without requiring the assistance of and interpretation by a technician. Because there is at least one control test in each column, the doctor can immediately assess whether the tests have been done correctly and thus have a high degree of confidence in any result which shows the presence or absence of the pathogen indicator under consideration. Additionally, because the tests can be conducted rapidly, a doctor may be able to have tests performed at relatively short time intervals and soon thereafter be able to see if the concentration of pathogen indicator is increasing or decreasing.

Figure 4:
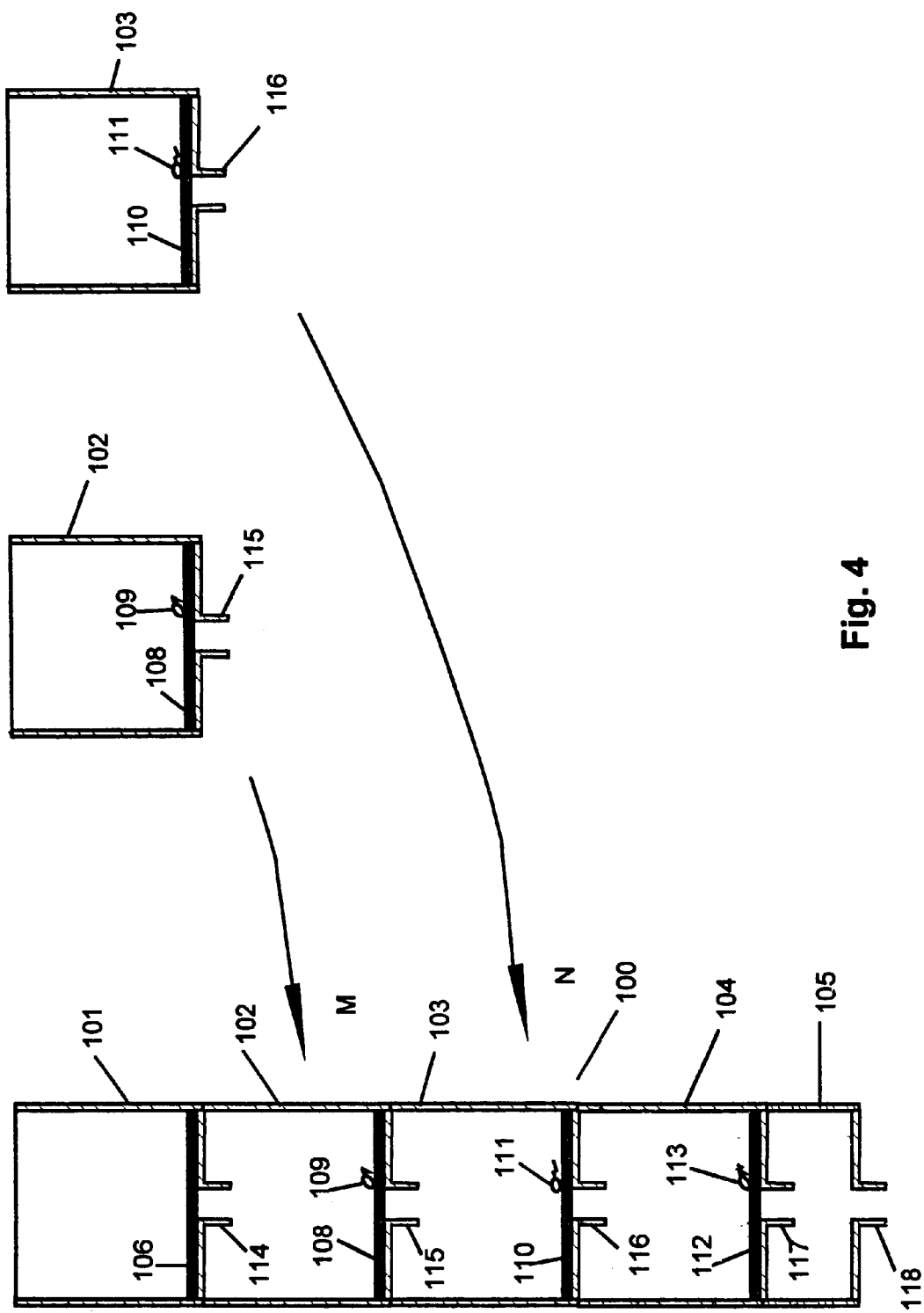
FIG. 4 shows a column made with four chambers.

Another arrangement of the column is shown in FIG. 4. Column 100 is constructed from four chambers 101, 102, 103 and 104 and a discharge chamber 105. Discharge chamber 105 has a discharge spout 118. Chambers 102 and 103 are shown to the right of completed column 100, with arrows M and N to show the placement of chambers 102 and 103 in the column. As shown in FIG. 4, the snares are spatially separate one from another so that there is an intervening air space between the snares. There are means to assure that chamber 102 can only be connected to the bottom of chamber 101, that chamber 103 can only be connected to the bottom of chamber 102, and that chamber 104 can only be connected to the bottom of chamber 103. One suitable example for ensuring connection among different chambers with correct order is to have embedded slots at a specific position for different chambers, or to have different numbers of slots for different chambers.

In the embodiment shown in FIG. 4, chamber 101 has a drain 114, a snare 106 which has no capture material thereon. Chamber 102 has a drain 115, and a snare 108 with a first control capture material 109. Chamber 103 has a drain 116 and a snare 110 with a pathogen indicator capture material 111. Chamber 104 has a drain 117, and a snare 112, with a second control capture material 113. The significance of the four chambers with their associated capture materials will be described hereinafter, particularly in relation to a pathogen indicator detection method using DNA. The presence of drain 114, 115, 116 and 117 is optional. When the snare is made of glass frit with appropriate pore size, there is no need of a drain. Such a snare is shown in column 120 of FIG. 8 and column 140 of FIG. 9A. On the other hand, if a membrane is used as a snare, a solid support is needed and a drain can be preferred.

In some countries, used columns must be discarded rather than being reused, whereas in other countries reuse of columns is permitted. In situations where reuse is permitted, an automated cleaning process is preferred in order to assure that the columns are not contaminated or otherwise inoperative. In such a process, the used column is washed with a reagent that destroys everything except the capture materials on the snares. After such washing, the column is tested for the presence of unwanted materials. If there are still unwanted materials on the column, then further washing and detection sequences are carried out. If, after a number of washings, a particular column is still not clean, the column is discarded and replaced by a new column.

Figure 11:
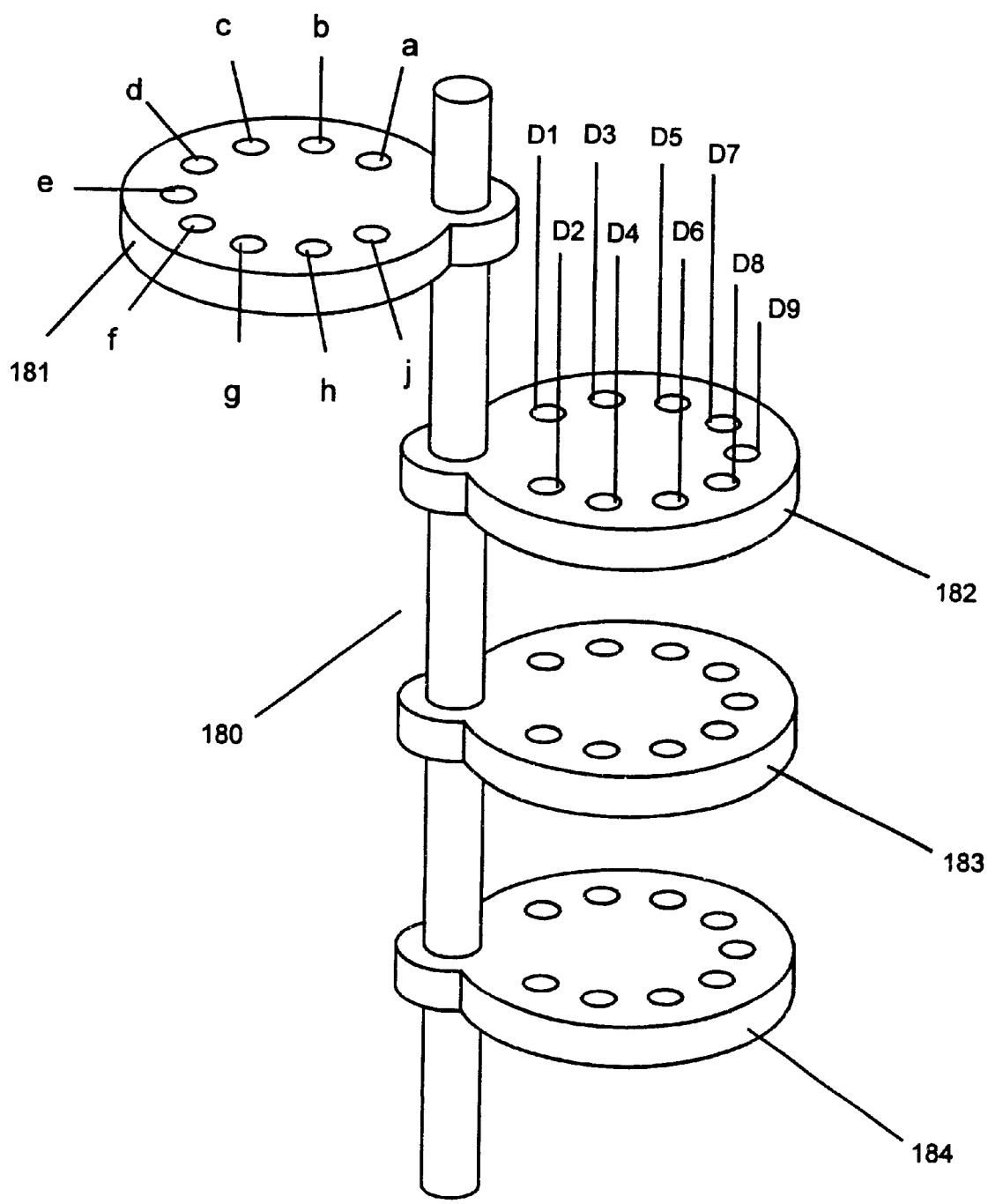
FIG. 11 shows a snare tray ensemble comprising a longitudinal stem and a plurality of snare tray which has a plurality of snares on each tray.

FIG. 11 illustrates a snare tray which provides an alternative ensemble of snares for detecting a test material. There is a stem 180 with a plurality of snare trays 181, 182, 183 and 184. Each snare tray has a plurality of snares thereon, e.g. a, b, c, d, e, f, g, h and j on tray 181, which may be viewed as equivalent to a column. Snares a and b for example may be for detection of positive and negative control materials, leaving snares c to j for detection of seven different pathogen indicator materials. The snares may be subjected to methods of binding, labelling and detection substantially as described hereinbefore. Because the snares on any one tray are in a plane transverse to the longitudinal direction of the stem 180, detection is best performed by placing the detectors above the trays. For example, detection may be made with detectors D1 to D9. In the embodiment shown in FIG. 11, it will be understood that detection of the materials on snare 181 has been completed and tray 181 has been swung out of the way of detectors D1 to D9. Detectors D1 to D9 are in position for detecting capture and labelled materials on the snares of tray 182. Thus each tray is adaptable to detection of a large number of materials, e.g. pathogen indicators, with a single tray.

Another aspect of the invention provides a method for detecting the presence of a protein in a test sample. The method comprises the steps of:

(a) adding a sample and a control material to a column wherein the column has at least two snares, one of said snares having thereon a first control capture material for binding to the control material; at least one of said snares thereon having a target capture material for binding to the target protein in the test sample for which detection is being sought, so that the control material binds with the first control capture material to form a bound control material, and target protein present binds with the test capture material;

(b) adding a wash solution to the column to remove unbound control material and unbound target protein;

(c) adding a labelling material to the column, to bind with the control material and bound target protein;

(d) adding a wash solution to the column to remove unbound labelling material; and (e) detecting any detectable signals from the labelled and bound control material and from any labelled and bound target protein.

The method can further include adding a substrate which reacts with the labels to give off detectable signals. The control material can be added into the column separately from the test sample. Alternatively, the control material can be added into the test sample prior to addition of the sample into the test column.

The target protein in the above process includes antigen, antibody and other proteins. When the target protein is an antigen, the capture material is an antibody which specifically binds to the target antigen. The labeling material can be a primary antibody, which binds to the bound target antigen, having thereon a chemical or enzyme label. Furthermore, the above described process is not limited to protein analysis. When a test material is capable of binding to a capture material specifically, the method can be applied.

Figure 5A:
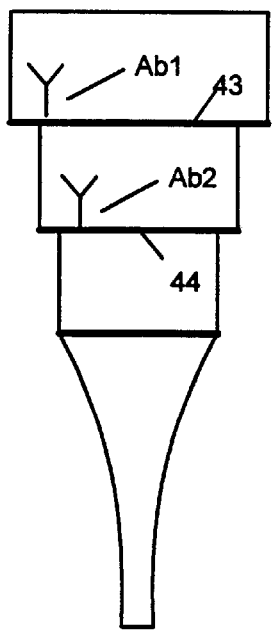
FIGS. 5A, 5B and 5C show a process of one embodiment of the present invention, schematically.
Figure 5B:
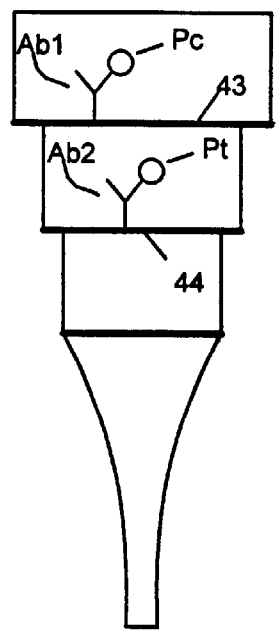
Figure 5C:
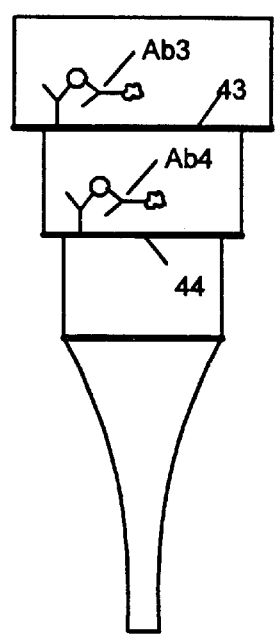

One process falling within the scope of the invention is now described with respect to a protein detection in a serum sample. FIGS. 5A, 5B and 5C generally show the process in simplified terms, in which there is detection of a control protein Pc, e.g. albumin, and a protein Pt whose presence is being tested for, e.g. a tuberculosis protein. The control protein Pc is present in the serum and it is not known whether the tuberculosis protein Pt is present in a patient serum sample. With reference to FIG. 1, therefore, the control protein Pc is already inherently in the sample in test tube 19 or had been deliberately added into the sample beforehand. Alternatively, the control protein Pc can be added into the column separately from the patient sample, either prior to or after addition of the patient sample. Snare 43 is a sintered glass frit which has a first capture antibody Ab1 attached thereto, and snare 44 is a sintered glass frit which has a second capture antibody Ab2 attached thereto, as shown in FIG. 5A. Snares 43 and 44 are in the same column and are indexed to the window 17, so that the column is in the position 18 (see FIG. 1). As indicated, the serum which is in test tube 19 contains the control protein Pc. For the purposes of this illustration, it is assumed that the protein Pt which is to be tested for, e.g. a tuberculosis protein, is present. A technician transfers an aliquot of serum from test tube 19 into the top of column 18 and the conveyor then indexes the conveyors so that the column is moved to the first reagent station. As it does so, the serum travels through snares 43 and 44. Control protein Pc binds to the first capture antibody Ab1 on snare 43, and the protein Pt binds to the second capture antibody Ab2 on snare 44, as shown in FIG. 5B. At the first reagent station, a wash is administered to the column. The purpose of the wash is to remove any excess serum, including unbound control protein Pc and protein Pt.

It will be understood that transfer of serum to the column may also be automated. At the time of transfer of the serum to the column, the correlation of the identity of the serum test tube and the corresponding column are noted, either by the technician, e.g. by typing identification numbers into a computer, or by automatic methods such as bar coding of test tubes and columns.

After washing at the first reagent station, the column is then indexed to a second reagent station. At the second reagent station, a primary antibody Ab3 which will bind to the control protein Pc, is added to the column. Primary antibody Ab3 has, for example, a chemiluminescent label. After indexing to a third reagent station, a primary antibody Ab4 which will bind to the protein Pt, is added to the column, as shown in FIG. 5C. Primary antibody Ab4 also has, for example, a chemiluminescent label. The column is then indexed to a fourth reagent station which is a wash station. The wash removes any excess primary antibodies Ab3 and Ab4. It is preferable that antibodies Ab3 and Ab4 are the same, in which case only one reagent station is required for the primary antibody.

The column is then indexed to a fifth reagent station which is also adjacent to a detector block. At the fifth reagent station a trigger solution is added to the column. The trigger solution reacts with the labels of the primary antibodies Ab3 and Ab4. Assuming that the reactions are chemiluminescent, there are emanations of light from each of the snares 43 and 44. The light signal from snare 43 is then detected by detector 50 and the light signal from snare 44 is detected by detector 51. Light from snare 43 indicates the presence of the control protein Pc on the snare and light from snare 44 indicates the presence of the protein Pt on the snare.

It will be appreciated from the above discussion that if there is no protein Pt in the serum, then obviously there can be no binding of such protein to capture antibody Ab2. Thus there would be nothing for primary antibody Ab4 to react with and so there would be no chemiluminescence detected by detector 51.

The advantage of using the control protein Pc is that if there is no signal detected by detector 50 after adding the trigger solution, then it indicates operation errors. If there is a signal from the control protein Pc, then the person analyzing the results can be reasonably assured that an absence of signal from snare 44 truly indicates that either no protein Pt present in the serum, or the protein Pt concentration is below the detection limit.

The control protein may be a protein that is always present in a serum sample, e.g. albumin, or a control protein may be added deliberately to the serum, or into the column directly.

It is sometimes desirable to have a second control protein (P2), which would be used to indicate whether all of the steps in the process have been carried out. For example, snare 45 may have a third capture antibody Ab5 (not shown) thereon. After addition of the serum, with the first control protein Pc and possibly the protein Pt, and washing of the column, the second control protein P2 may be added. Second control protein P2 would bind to third capture antibody Ab5. Third capture antibody Ab5 may be activated by addition of a primary antibody Ab6 which has a label, e.g. a chemiluminescent label. Now, instead of adding a reagent which only has primary antibodies Ab3 and Ab4 as described in previous paragraphs, a reagent which has primary antibodies Ab3, Ab4 and Ab6 is added to column 40. After washing and addition of a trigger solution, any reaction with primary antibody Ab6 would be detected by detector 52. It should be noted that the second control protein may be added to the column together with the first control protein instead of separately, if desired.

It will be appreciated that if there is no detection of the second control protein P2, it can be safely assumed that the primary antibodies Ab3 and Ab4 were not added to the column. Thus there is a further indication of whether the complete analytical process has been performed properly.

Although described above in relation to detection of pathogen indicators in serum samples, the above method may be adapted for detection of viruses or chemicals such as drugs, carcinogens, explosives, opiates, pollutants.

Figure 6:
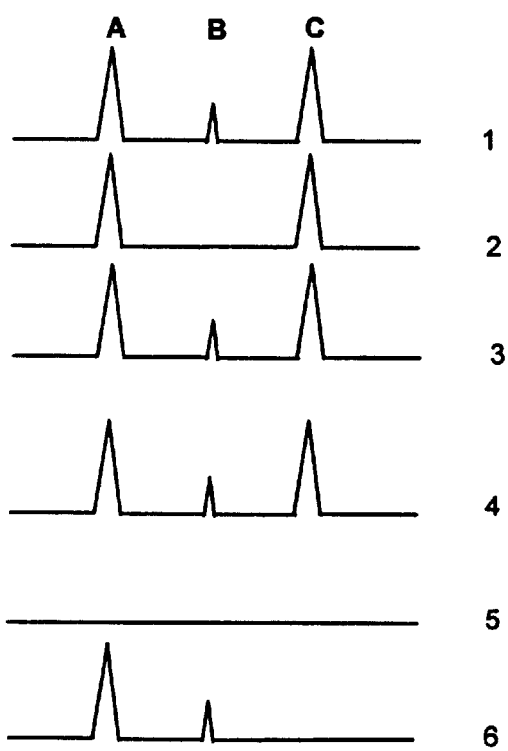
FIG. 6 shows read-outs from analyses of six samples using the method of the present invention, wherein each sample is analyzed with two controls. In the figure, A is the signal of a positive control, C is the signal of a negative control, and B is the signal of a test sample.

FIG. 6 shows the results of a method used where there are two control snares A and C and a snare B, which is used to detect for the presence of a particular pathogen indicator. In FIG. 6, six samples are tested in columns 1–6. Sample columns 1, 2, 3 and 4 show the presence of both control proteins, thus indicating that the serum is present, and that the correct primary antibodies for the first control and pathogen indicator were added. Sample columns 1, 3 and 4 show the presence of the pathogen indicator in snare B, whereas in sample 2 there is no pathogen indicator detected. Because both the control signals are positive, the operator can be reasonably assured that the lack of a signal for the pathogen indicator, in sample column 2 indicates that there is indeed no pathogen indicator present. In sample 5, neither of the control signals appear, indicating that the sample column never contained any control protein and thus lack of signal for snare B is meaningless. The negative result could be false.

In sample 6, the second control is not present. This indicates that the correct primary antibodies for detection of the first control and the pathogen indicator were not added. Thus sample 6 gives a false indication of the presence of the first control and the pathogen indicator. Detection of materials on the snares A and B has been detected, which may or may not be the first control and the pathogen indicator. Therefore, sample 6 is also meaningless.

The advantage of the present invention over prior methods is that sample 5 in prior methods would have been counted as a definite negative, i.e. it is a false negative for snare B and that sample 6 in prior methods would have been counted as a definite positive, i.e. it is a false positive for snare B.

A further aspect of the present invention provides a method for detecting the presence of a DNA sequence in a test sample. The method comprises the steps of:

(a) denaturing a test sample to form a single strand target DNA sequence for which detection is being sought;

(b) introducing the test sample and a first single strand control DNA sequence into a test column, wherein the column has at least two snares, one of said snares having thereon a first control single strand capture DNA sequence; at least one of said snares thereon having a target single strand capture DNA sequence specific to the corresponding target DNA sequence in the test sample; and wherein the target single strand capture DNA sequence will bind with the corresponding target DNA sequence in the test sample to form a double strand control DNA sequence; and the first control single strand capture DNA sequence will bind with the first control DNA sequence to form a double strand control DNA sequence;

(c) adding a wash solution to the column to remove unbound DNA;

(d) adding an enzyme to the column to destroy any single strand DNA;

(e) adding a denaturing solution to separate the formed double strand DNA sequences, then adding a wash solution to remove denatured non-capture single strand sequences, so that the single strand capture DNA sequences re-form on each snare;

(f) adding DNA probes to provide detectable labels for single strand capture DNA sequences formed in step (e);

(g) adding a wash solution to the column to remove unbound DNA probe; and (h) detecting any signals from each snare.

The method can further include adding a substrate which reacts with the labels to give off detectable signals. The first single strand control DNA sequence can be added into the test sample prior to introducing the sample into the test column, or can be added into the test column separately from the test sample. The method further comprises introducing a second single strand control DNA sequence into the test column; wherein the test column also has a control snare having thereon a second control single strand DNA capture sequence. With the method of the present invention, one single snare can also have more than one single strand capture DNA sequences thereon. In this case, the labels are different for different single strand capture DNA sequences on one single snare so that different DNA sequences can be detected on one single snare.

Figure 7:
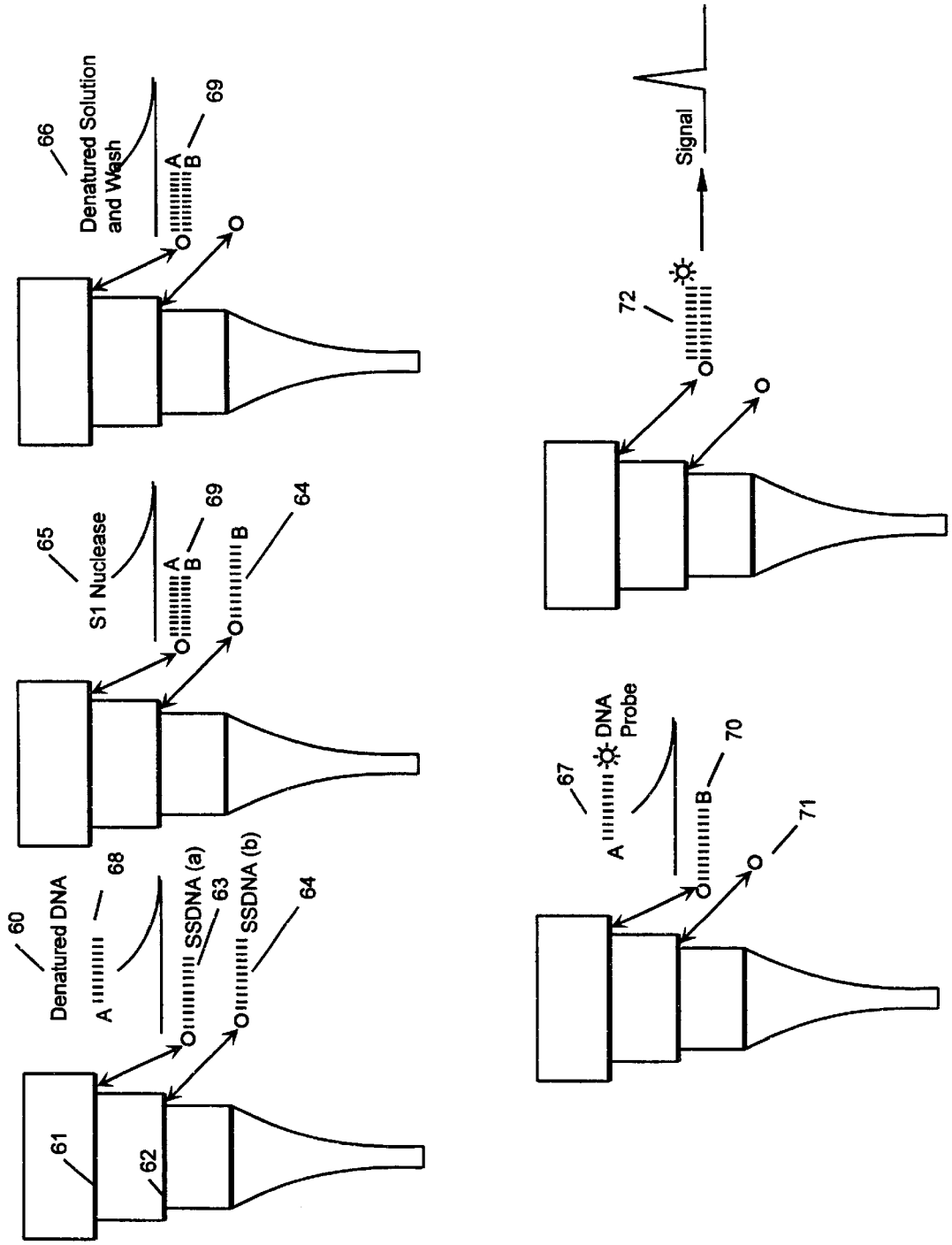
FIG. 7 illustrates a method for detecting a DNA sequence in a sample.

FIG. 7 shows the use of the above described method for DNA analysis. In this particular embodiment it is not necessary to amplify the DNA using, for example, PCR techniques. Single strand synthetic DNA (SSDNA(a)) for the control (control single strand capture DNA sequence) and single strand DNA (SSDNA(b)) for the target pathogen indicator (target single strand capture DNA sequence) are provided in the column on snares 61 and 62, to provide the equivalent of the capture materials (shown by 63 and 64 respectively in FIG. 7) discussed previously.

The patient sample is prepared so that the DNA, if present, has been isolated. The isolated target DNA as well as the control DNA are denatured into single strand DNA form and then are applied to the column (shown by 60 in FIG. 7). The control DNA and the target DNA if present will bind specifically to the single strand control capture DNA sequence and the target single strand capture DNA sequence, respectively. The denatured control DNA and the target DNA in the patient sample is equivalent to the control protein and the target protein respectively in reference to FIGS. 5A to 5C.

The column is washed to remove non-binding DNA. An enzyme that specifically destroys single strand DNA and RNA, such as S1 nuclease 65, is then added to the column. As is known, S1 nuclease destroys only single strand DNA and RNA, not double strand DNA or RNA/DNA complex. Therefore if there has been no combination of either the SSDNA(a) or SSDNA(b), the single strand DNA will be destroyed. However, if either SSDNA(a) OR SSNDA(b) has been combined to form double strand DNA, the double strand DNA will not be destroyed. Following a washing step, a further denaturing solution 66 is added to the column. This denaturing solution separates any double strand DNA into single strand DNA. The column is again washed.

Following washing, labelled DNA probes for the control and target DNA, are added to the column. Preferably, a single labelled DNA probe 67, suitable for both control and target DNA is used. Finally, the column is washed to remove any non-binding probes. The presence of any labelled DNA probes is then detected using appropriate detection means, for example, with trigger solution and detectors.

In the process illustrated by FIG. 7, the denatured sample 60 only has denatured control DNA 68 therein. There is no target pathogen indicator present. Therefore only SSDNA(a) 63 is annealed with control single strand DNA 68 to form double strand DNA 69. Because there is no denatured target DNA, SSDNA(b) remains as a single strand. Therefore, after addition of S1 nuclease, SSDNA(b) is destroyed, leaving only control double strand DNA 69. Control double strand DNA 69 is denatured with denature solution 66, leaving single strand DNA 70 (which is the same as SSDNA(a)). There is no single strand target DNA to denature (71). Finally a labelled DNA probe 67 is added, which forms a double strand control DNA 72, which may then be detected. In this instance, only the control DNA would be detected because there was no target DNA present.

In a further embodiment, the present invention provides another method for detection of DNA sequence in a test sample. The method comprises:

(a) providing a positive control single strand DNA sequence;

(b) denaturing a test sample to form a single strand target DNA sequence;

(c) adding the test sample and the positive control DNA sequence to a test column, wherein the column has at least two snares, one of said snares having thereon a first control single strand capture DNA sequence for binding to a portion of the positive control DNA sequence; at least one of said snares thereon having a target single strand capture DNA sequence specific to the corresponding target DNA sequence in the test sample, so that the positive control DNA sequence binds with the first control single strand capture DNA sequence wherein the bound the positive control DNA sequence has a double strand portion and a single strand portion; and the target DNA sequence present in the test sample binds with the target single strand capture DNA sequence wherein the bound the target DNA sequence has a double strand portion and a single strand portion;

(d) adding a wash solution to the column to remove unbound DNA;

(e) adding DNA probes to provide detectable labels for attachment to the single strand portion of the bound positive control DNA sequence and the single strand portion of the bound target DNA sequence formed in step (c);

(f) adding a wash solution to the column to remove unbound DNA probe; and (g) detecting any signals from each snare.

The method can further include adding a substrate which reacts with the labels to give off detectable signals. The positive control single strand DNA sequence is prepared from a target DNA sequence for which detection is being sought, by a process selected from the group consisting of (1) inserting a control DNA fragment into the target DNA sequence for which detection is being sought at a predetermined scission point; and (2) removing a small fragment of DNA from the target DNA sequence at a predetermined scission point;

Moreover, the method can further include adding a negative control DNA sequence to the test column. In this case, the test column also has a control snare having thereon a second control single strand capture DNA sequence for binding to the negative control DNA sequence, so that the negative control DNA sequence binds with the second control single strand capture sequence to form a bound negative control DNA sequence. The negative control single strand DNA sequence is different from the target DNA sequence and different from the positive control DNA sequence.

The control DNA sequences can be added into the test column separately from the test sample, or can be added into the test sample prior to the addition of the test sample to the test column.

Figure 8:
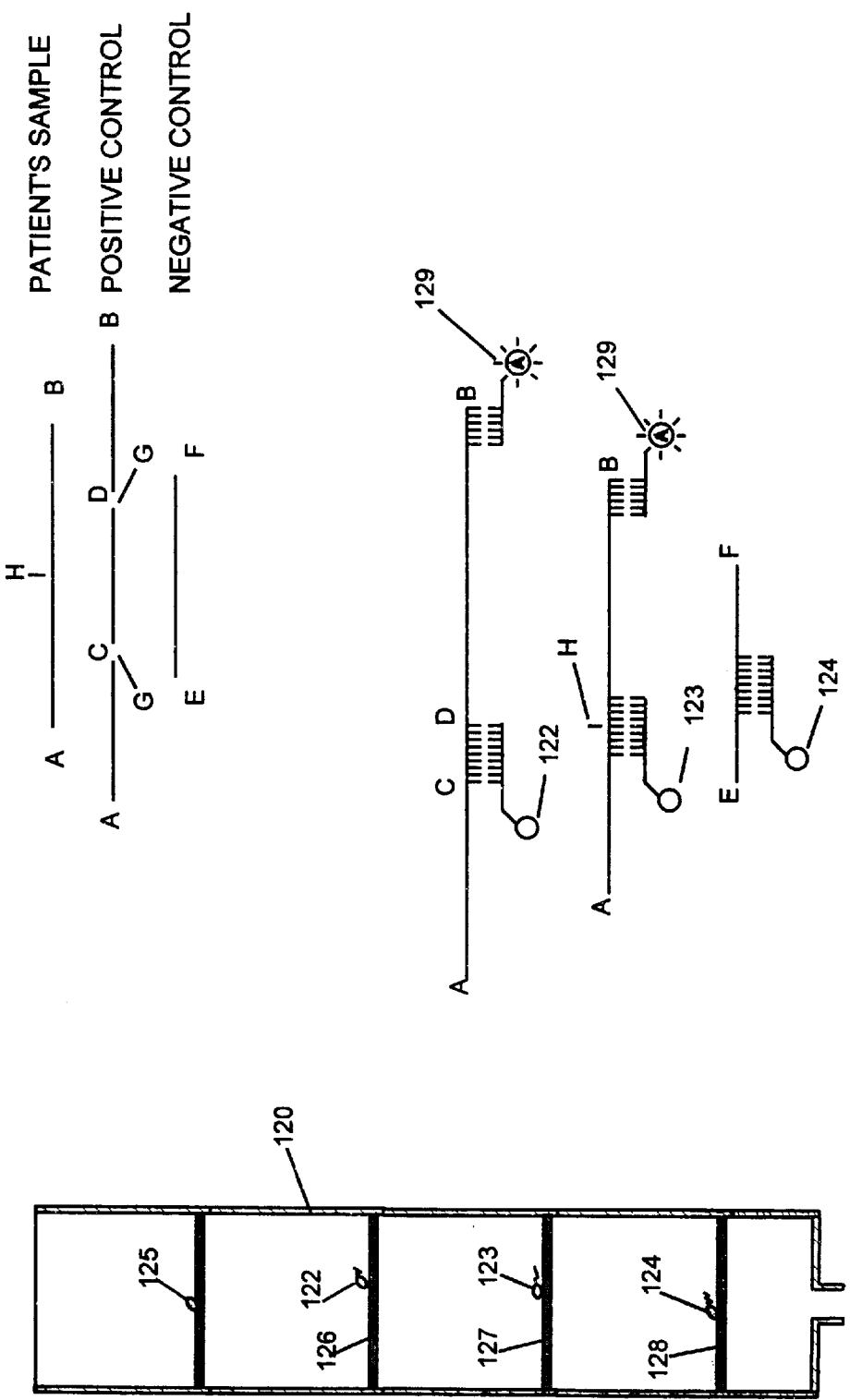
FIG. 8 illustrates another method for detecting a DNA sequence in a sample.

This method is exemplified in FIG. 8. A target DNA sequence, for which detection is sought, is selected, e.g. tuberculosis DNA sequence. A mutation is formed by known techniques of insertion of a DNA sequence or deletion of a portion of the target DNA sequence. For example, in relation to FIG. 8, such a mutated target DNA is referred to as a positive control. The target DNA has a sequence A-B. In the embodiment shown in FIG. 8, the positive control is created by inserting a synthetic DNA fragment C-D, e.g. a base of 100 nucleotides, into the target sequence A-B, at scission point G. A negative control is also created, which is a synthetic DNA fragment E-F, of which the sequence is not present in the target DNA that is sought to be detected.

For example, a segment of target DNA, of about 300 bases is selected, cloned and confirmed by DNA sequencing. Based on that cloned DNA, a small fragment of about 100 bases of non-target DNA is inserted into the middle of the cloned DNA as the positive control DNA. A non-target DNA of about 200 bases is also selected, cloned and confirmed by DNA sequencing and is used as a negative control DNA. When the tests are carried out, the patient sample is added to a test tube which also contains at least the positive control, and can contain the negative control.

In a variation of the above method, the positive control may have a small fragment of DNA (about 100 bases) cut away from the target DNA.

For the purpose of the illustration in FIG. 8, it is assumed that the patient has the pathogen indicator DNA, e.g. tuberculosis, which is sought to be detected. For a sample with the patient's DNA, A-B, a positive control DNA sequence A-C-D-B and a negative control DNA sequence E-F are prepared. All DNA sequences are denatured so that the patient's DNA, positive control and negative control are in single strand DNA form.

A test column 120 is prepared which has three single strand capture DNA materials. The positive control capture DNA 122 has a sequence which will bind specifically to the inserted DNA fragment C-D. The target capture DNA 123 has a sequence which will bind to the target DNA A-B on both sides of where the scission point is in the positive control DNA (point H in target DNA A-B). More specifically, point H in the target DNA sequence and the scission point G in the positive control are the same. The negative control capture DNA 124 has a sequence which will bind specifically to synthetic DNA fragment E-F. AS shown in FIG. 8, positive control capture DNA 122, target capture DNA 123 and negative control capture DNA 124 are on snares 126, 127 and 128 respectively. There is a fourth snare 125 which has no DNA attached thereto. The purpose of snare 125 is for determining background "noise" in the sample. Snares 125, 126, 127 and 128 are separated longitudinally along column 120.

When performing the test for the sample, which comprises the patient's sample (target DNA, if present) and the positive and negative controls, the sample is allowed to enter column 120. It will be understood that if there is any positive control DNA A-C-D-B in the sample, it will bind with positive control capture DNA 122 with sequence C-D, leaving a sequence adjacent B, for example, free for binding to a single strand DNA probe (129). If there is any target DNA A-B in the sample, it will bind with target capture DNA 123 about scission point H, leaving a sequence adjacent B, for example, free for binding to a single strand DNA probe (129). If there is any negative control DNA E-F in the sample, it will bind with negative control capture DNA 124. Of course, if there is no target DNA A-B present, target capture DNA 123 will remain unbound. It will be understood that the positive and negative controls can be directly added into the test column separately from the patient sample.

After passing the sample through column 120, the snares are washed to remove excess single strand DNA which has not bound to any of the capture materials. After washing, a synthetic single strand DNA probe 129, which can bind with an unbound portion of the target sequence A-B, is passed through column 120. As shown in FIG. 8, the sequence is close to position B. Probe 129 will attach itself to positive control DNA A-C-D-B or target DNA A-B that is present, for example at the common end sequence adjacent B, as shown in FIG. 8. This method provides advantages by sharing a common sequence between the control and the target DNA for the probe binding. One advantage is that a common probe sequence can be used for both control and the target DNA. In the method illustrated by FIG. 7, two different probe sequences need to be used. Furthermore, in the method demonstrated by FIG. 8 the specificity and affinity of probe binding are the same between the control and the target DNA. The common reaction mechanism provides a better control for the detection process.

There is no binding of probe 129 to negative control DNA E-F because the negative control DNA E-F does not share the sequence of probe 129. Probe 129 has a detection label thereon which is used to detect the presence of the probe. If there is no detection signal associated with snare 126, then there is no positive control DNA A-C-D-B in the column. The absence of positive control signal can indicate operation errors. If there is a detection signal associated with snare 128, then the probe has bound to a material that should not have been present and the test is suspected for potential problems.

Although the negative control is a secondary control, it provides important information in addition to that obtained from a positive control. Under normal condition, the snare for negative control should never produce signals. If a signal is detected from a negative control snare, it may indicate several potential problems. For example, (1) the probe is not specific enough; (2) the column is blocked or a wash cycle is not complete; (3) wash solution is contaminated; or (4) the sample is contaminated such as an increased fluorescein concentration due to specific type of food or drug taken by the patient. Some of these could also be detected on snare 125, if it is used.

Alternatively, with the method of FIG. 8 one single snare can also have thereon more than one single strand capture DNA sequences. In this case, the control and the test DNA can not share a common sequence for probe binding if they are on the same snare. The probes and labels for the control and for different target DNA are also different so that different DNA sequences can be detected on one single snare.

As indicated hereinbefore, it is possible that the signals detected from the control DNA materials and any target DNA material can be subject to some background interference caused by interaction of other materials in the sample with the snare material. The background interference can be detected from snare 125 which is independent of the control DNA materials or the target DNA material. The signals obtained from detection of the control DNA materials or the target DNA material can therefore be adjusted accordingly to take into account the interference.

The possible results are shown in Table 1 below:

TABLE 1

| Test | Positive control | Target | Negative control | Result |
|---|---|---|---|---|
| Test 1 | Positive | Positive | Negative | target DNA present |
| Test 2 | Positive | Negative | Negative | target DNA not present |
| Test 3 | Positive | Positive | Positive | Test is false positive |
| Test 4 | Negative | Negative | Negative | Test is false negative |

Thus, it can be seen that the test gives a high degree of confidence of the presence or absence of the pathogen indicator for which the test was made.

In situations where re-use is permitted, when it is desired to re-use the columns in the DNA method, the columns can be cleaned by passing a denaturing solution through the column. This causes the capture materials to revert to the single strand capture materials. Then the column is subjected to labelled probes, which should bind only with a bound target material, not capture material, and trigger chemicals and detection of any reaction. Normally, there would be no reactions detected and the column can then be washed ready for re-use. If any reaction is detected, then further treatment with denaturing solution would be used. This recycling process can be used with the DNA analysis method illustrated in FIG. 8.

In another aspect, the present invention also provides a method for detection of RNA in a test sample. In previously known methods, it is necessary to isolate the RNA and convert the RNA into cDNA. This leads to loss and/or degradation of the RNA. Sometimes the loss of RNA is greater than 90%. The present method overcomes this problem and provides a greatly enhanced efficiency in the present test method in which very little, if any, RNA is lost. Additionally, as described in relation to the other embodiments of the invention, there is an increase in the reliability and accuracy of the test.

A method for detecting the presence of a RNA sequence in a test sample comprises the steps of:

(a) providing a positive control single strand DNA sequence;

(b) adding the test sample and the positive control DNA sequence to a test column wherein the column has at least two snares, one of said snares having thereon a first control single strand capture DNA sequence for binding to the positive control single strand DNA sequence; at least one of said snares thereon having a target single strand capture DNA sequence specific to the corresponding target RNA sequence in the test sample, so that the positive control DNA sequence binds with the first control single strand capture DNA sequence to form a double strand positive control DNA sequence, and the RNA sequence present in the test sample binds with the target single strand capture DNA sequence to form a double strand DNA/RNA complex;

(c) adding a wash solution to the column to remove unbound positive control DNA and target RNA;

(d) adding an enzyme to the column to destroy single strand DNA and RNA;

(e) adding a denaturing solution to separate the formed double strand control DNA sequence and double strand DNA/RNA complex, then adding a wash solution to remove denatured non-capture single strand DNA and RNA sequences, so that the single strand capture DNA sequences reform on each snare;

(f) adding DNA probes to provide detectable labels for single strand capture DNA sequences formed in step (e);

(g) adding a wash solution to the column to remove unbound DNA probe; and (h) detecting any signals from each snare.

The method can further include adding a substrate which reacts with the labels to give off detectable signals. There are different modes for practising the RNA detection method. In one mode, the positive control single strand DNA sequence is different from the target RNA sequence and the first control single strand capture DNA sequence is different from the target single strand capture DNA sequence. In addition, the DNA probes used in step (f) are different for the first control capture and the target capture sequences.

In another mode, the positive control single strand DNA sequence has a portion which has the same sequence to a portion of the target RNA sequence. The first control single strand capture DNA and the target single strand capture DNA have a common sequence at a portion of the capture sequences, so that a common DNA probe is used in step (f) for detection of the re-formed control and target capture sequences.

Furthermore, step (a) of the RNA detection method can further include providing a negative control single strand DNA sequence which is different from the target RNA sequence and different from the positive control DNA sequence. In this case, step (b) further includes adding the negative control DNA to the test column which also has a control snare having thereon a second control single strand capture DNA sequence. The second control capture DNA sequence partially matches the negative control DNA sequence so that the negative control DNA sequence binds with the second control capture DNA sequence to form a double strand DNA sequence which also has unbound single strand portions. Step (f) DNA probes do not match re-formed partial second control single strand capture DNA sequence formed in step (e), and no binding occurs between them. Therefore, in step (h) no signal is detected from the second control snare under normal conditions.

There are also different modes for using a negative control. In one mode, the second control single strand capture DNA sequence is different from the target capture DNA and the first control capture DNA sequences.

In an alternative mode, the first control capture DNA, the second control capture DNA and the target capture DNA have a common sequence at a portion of the capture sequences. A common DNA probe is used in step (f) for detection of the re-formed control and target capture sequences.

Figure 9:
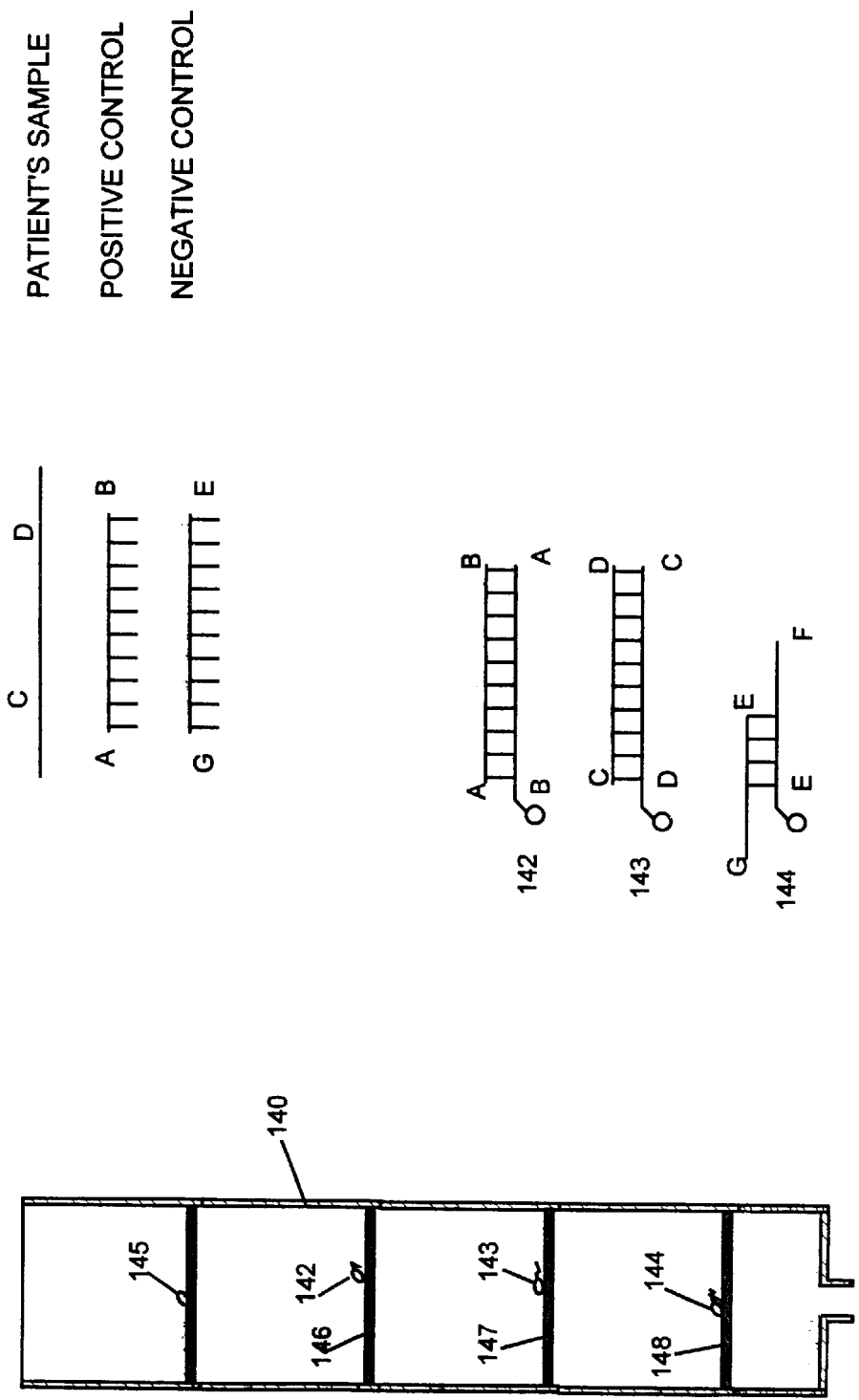
FIGS. 9A and 9B illustrate two modes of a method for detecting a RNA sequence in a sample.

One mode of RNA detection process of the present invention is shown schematically in FIG. 9A. Positive and negative controls are synthesized. For example, positive control DNA A-B and negative control DNA G-E are synthesized. Both of them are single strand DNA sequences. But the nucleotide sequences for the positive and negative controls are different from in the target RNA C-D.

A test column 140 is prepared which has three single strand capture DNA materials. The positive capture DNA 142 has a sequence which will bind specifically with positive control sequence A-B. The target capture DNA 143 has a sequence which will bind to the target RNA C-D if present. The negative control capture DNA 144 has a sequence E-F which will partially bind, e.g. 30–70% bind, to the negative control sequence G-E, i.e. the bound (double) strand is shorter than either of the single strand G-E sequence or the E-F sequence. As shown in FIG. 9A, positive control capture DNA 142, target capture DNA 143 and negative control capture DNA 144 are on snares 146, 147 and 148 respectively. There is a fourth snare 145 which has no capture DNA attached thereto. The purpose of snare 145 is for determining background "noise" in the sample. Snares 145, 146, 147 and 148 are separated longitudinally along column 140.

When performing the test, the patient's sample (target DNA, if present) and the positive control is allowed to enter column 140. It will be understood that positive control DNA A-B will bind with positive control capture DNA 142 and if there is any target RNA C-D in the sample it will bind with target capture DNA 143. Of course, if there is no target RNA C-D present, target capture DNA 143 will remain unbound.

After passing the sample through column 140, the snares are washed, to remove excess single strand sequence which has not bound to any of the capture materials. The negative control DNA G-E is then allowed to pass through column 140. The sequence G-E will bind with target capture DNA 144. After washing, S1 nuclease is passed through the column. As S1 nuclease destroys single strand DNA, the single strand portions of negative control DNA G-E and negative control capture E-F, which are not bound to one another, will be destroyed. This will leave a small segment of double strand DNA from the negative control capture material. Clearly, if either of the other single strand capture materials (142 or 143) have not been bound, they too will be destroyed.

The column is washed again and the now double strand materials are denatured before being washed again. Subsequently, synthetic single strand DNA probes (not shown in the figure) are added to column 140 for the detection of any single strand positive control capture DNA 142 and single strand capture DNA 143 that is left in the column. The probes have detection labels thereon, which are used to detect the presence thereof. The mechanism of using single strand DNA probes for detection in the RNA analysis is the same as in the DNA analysis, which is illustrated in FIG. 7.

Also similar to the DNA analysis of FIG. 7, using the RNA detection method of FIG. 9A one single snare can also have more than one single strand capture DNA sequences thereon. The labels are different for different single strand capture DNA sequences on one single snare so that different DNA sequences can be detected on one single snare.

Figure 9B:
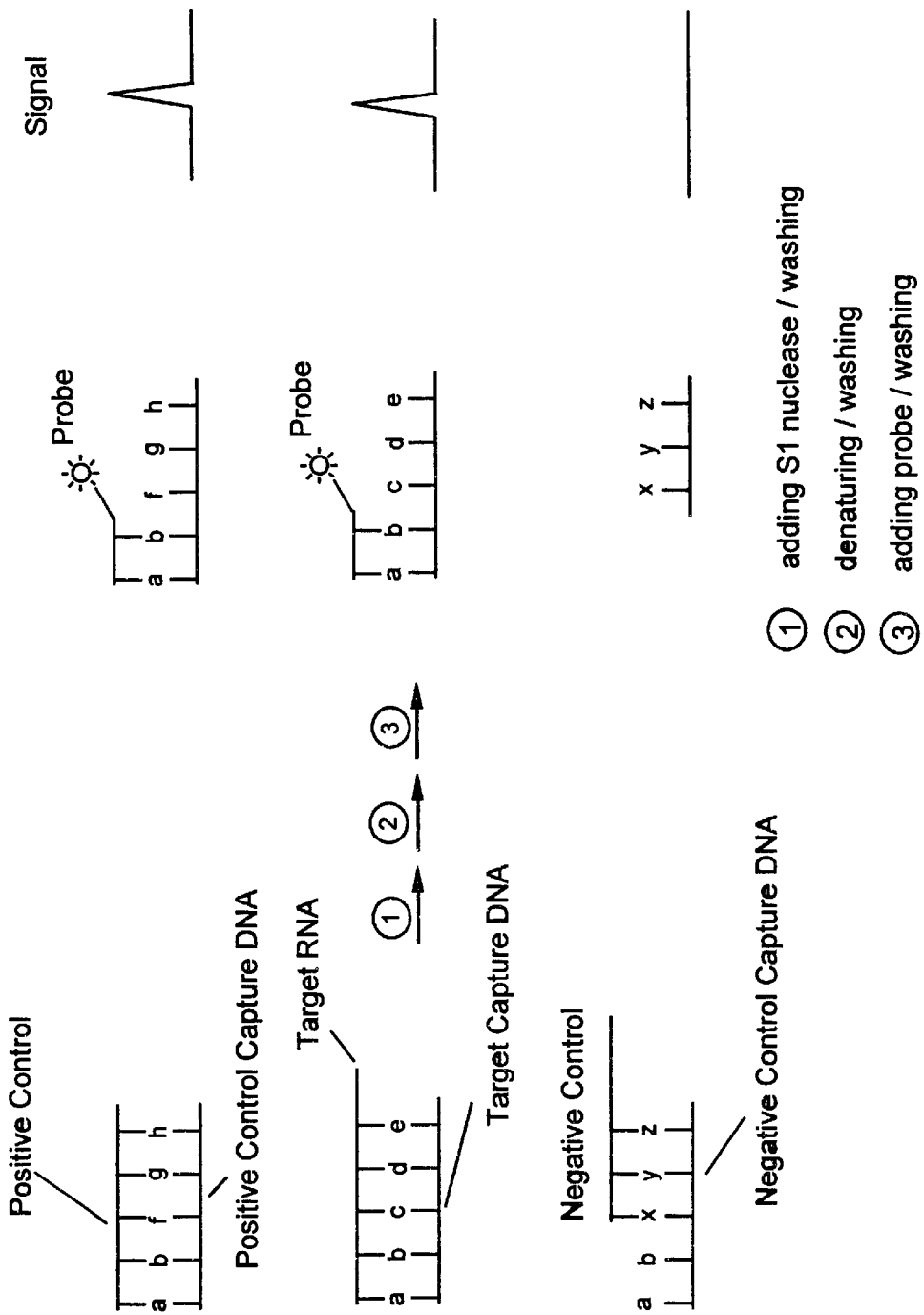

FIG. 9B shows another mode of the RNA detection method. The general concept of positive control and negative control stays the same to that described above in DNA and RNA detection. The method illustrated in FIG. 9B has a common single strand capture DNA portion, a-b, at one end of the three capture sequences used for capturing the positive and negative controls and the target RNA sequence, respectively. This is different from the method of FIG. 9A, where the negative control capture DNA sequence does not have a portion of its sequence being the same to a portion of the positive control and the target capture sequences. Follow the same process described above for FIG. 9A, after addition of S1 nuclease the common portion, a-b, of the negative control capture sequence should be destroyed by the enzyme and removed by a washing applied subsequently. Because the common portion, a-b, is an unbound single strand portion. A common probe with a label is applied after denaturing and final washing steps. The probe will bind to the common portion, a-b, of the re-formed positive control capture sequence, and the re-formed target capture sequence if the target RNA present in the sample. Signals will be detected on those snares. However, no signal should be detected on the snare thereon having the negative control sequence under normal operation conditions. Because the portion, a-b, of the negative control capture sequence would not be present then. In this case, if any signal above noise level is detected on the negative control snare, it indicates operation errors. All four possible errors discussed previously with the DNA detection method illustrated by FIG. 8 could present here also. In addition, in this case, the error could also be caused by the quality and efficiency of the S1 nuclease used. Therefore, as an advantage, this method can further indicate and control the reagent and the instrument operating conditions to ensure quality of the detection.

In FIG. 9B, for the convenience of illustration a common capture portion, a-b, is positioned at one end of the capture sequences. However, it is understood that a common portion can be at any position of the capture sequences. In addition, more than one common portion can present for the purpose of probe binding and subsequent detection.

A computer may be used to handle and display signals from the detectors. Additionally, a computer is preferably used to control indexing of the conveyors, activation of the introduction of reagents, control of the quantity of reagents added to the columns, and the cleaning stations if present. Use of a computer enhances the repeatability and reliability of the method. It will be understood that other control methods may be used, e.g. electromechanical methods.

An apparatus for dispensing a sample or a reagent into the column is shown in FIGS. 10A to 10C. The apparatus is also called a sample dispenser which comprises a sample holder 157 and a puncturer 151.

FIG. 10A shows a column 150 which comprises chambers 151, 152, 153 and 154. At the top 155 of upper chamber 151 there is a delivery spout 156 which is coaxial with the longitudinal axis of column 150. The upper chamber 151 is also called a puncturer. Separate from column 150 is a sample holder 157 which has an open lower end 158 and an upper end 159 which may be closed or have means for the introduction of air or other gas. Inside sample holder 157 is an annular disk 160 with a central bore which is sealed with a film, 162, wherein the film is capable of being punctured. The sample holder 157 contains reagent 161. Preferably, the inner diameter of sample holder 157 is marginally greater than the outer diameter of chamber 151. It is understood that although FIGS. 10A to 10C show a cylindrical shape for both test column and sample dispenser, alternatively, other shapes such as square or rectangular shapes should also work for both column and the dispenser as long as the bore and the spout fit appropriately.

In FIG. 10C, sample holder 157 is situated so that annular disk 160 is just above delivery spout 156. As sample holder 157 is lowered, the spout 156 is cause to puncture the film 162 and allow reagent 151 to flow into column 150, as will be seen in FIG. 10B. In the specific example given in FIGS. 10A to 10C, chamber 151 has dual functions, a puncturer which punctures the film 162 to dispense the liquid sample and a column connector which provides a connection between the sample holder and the column.

The Figures of the present specification show the columns in a vertical arrangement. It will be understood that the columns may be in a horizontal alignment. For example, with the chambers of a column may be placed side-by-side. In this case, a chamber having a control capture material on the snare can be placed next to each chamber having a test capture material on the snare. Therefore, a control and a test pair can be processed together. This configuration is more suitable when the binding process is less specific between the control with the control capture material and the test material with its capture material.

In another aspect, the present invention provides a kit which comprises (a) a column for analysis of a test material; and (b) reagents for detecting the presence of the test materials. The column in the kit has at least two snares, one of the snares having thereon a first control capture material for detecting the presence of a first control material, and the other snare having thereon a capture material for detecting a test material for which detection is being sought. The column in the kit can also have at least two chambers, each chamber having a snare, one of the chambers having a first control capture material on the snare for detecting the presence of a first control material, and the other chamber having a capture material on the snare for detecting a test material for which detection is being sought. The kit can also include wash solutions for removing excess reagents from the column.

As indicated herein, the method of the present invention has wide applicability. Areas of applicability include research and diagnosis relating to cancer, auto-immune diseases, infectious diseases, haemostasis and veterinary medicine. For example, the DNA method of the present invention may be used for diagnosis of *N. gonorrhoea, H. ducreyi, trepona pallidum*, human papillomavirus (HPV), herpes simplex virus (HSV), *molluscum contagiosum* (MC), *trichomonas vaginalis* and the RNA method may be used for diagnosis of human immunodeficiency virus (HIV).

It will be understood that multiple tests can be carried out in a single column merely by the addition of additional snares, capture materials and detection materials. For example, the test may be used simultaneously for certain proteins, DNA sequences and RNA sequences.

The invention has been described with reference to the preferred embodiments. It should be understood, however, that the invention is not so limited, and the scope of the invention should be determined with reference to the following claims, rather than to the foregoing specification.

What is claimed is:

1. A method for detecting the presence of a test material in a test sample comprises the steps of:
    (a) introducing a test sample and a control material into a test column, wherein the column has at least two snares, one of said snares having thereon a control capture material; at least one of said snares thereon having a target capture material specific to a corresponding test material in the test sample for which the detection is being sought, so that the control capture material will bind with the control material to form a bound control material; and the target capture material will bind with the corresponding test material to form a bound material; and wherein said snares are separate spatially one from another by an intervening air space so that said snares are not in contact with one another;
    (b) washing the test column to remove materials which have not been bound to the capture materials; and
    (c) detecting the presence of bound materials on each of the snares.

2. The method of claim 1, wherein said control material is introduced into the test column separately from the test sample.

3. The method of claim 1, wherein said control material is added into the test sample prior to introducing the sample into the test column.

4. The method of claim 1, wherein the method further comprises adding a label material for each of the bound materials to form labelled bound materials and then detecting the presence of the labelled bound materials.

5. The method of claim 1, wherein said test material is one member selected from the group consisting of DNA, RNA, PNA, antigen, antibody, protein and a material capable of binding specifically to one member selected from the group consisting of DNA, RNA and proteins.

6. A method for detecting the presence of a DNA sequence in a test sample comprises the steps of:
    (a) denaturing a test sample to form a single strand target DNA sequence for which detection is being sought;
    (b) introducing the test sample and a first single strand control DNA sequence into a test column, wherein the column has at least two snares, one of said snares having thereon a first control single strand capture DNA sequence; at least one of said snares thereon having a target single strand capture DNA sequence specific to the corresponding target DNA sequence in the test sample; and wherein the target capture DNA sequence will bind with the corresponding target DNA sequence in the test sample to form a double strand DNA sequence, and the first control capture DNA sequence will bind with the first control DNA sequence to form a double strand control DNA sequence;
    (c) adding a wash solution to the column to remove unbound DNA;
    (d) adding an enzyme to the column to destroy single strand DNA;
    (e) adding a denaturing solution to separate the formed double strand DNA sequences, then adding a wash solution to remove denatured non-capture single strand sequences, so that the single strand capture DNA sequences re-form on each snare;
    (f) adding DNA probes to provide detectable labels for single strand capture DNA sequences formed in step (e);

(g) adding a wash solution to the column to remove unbound DNA probe;

(h) detecting any signals from each snare.

7. The method of claim 6, wherein the method further includes adding a substrate which reacts with the labels to give off detectable signals.

8. The method of claim 6, wherein the first single strand control DNA is added into the test column in one way selected from the group consisting of (1) separately from the test sample, and (2) being added into said test sample prior to introducing the sample into the test column.

9. The method of claim 6, wherein step (b) further comprises introducing a second control single strand DNA sequence into the test column; wherein the test column also has a control snare having thereon a second control single strand capture DNA sequence.

10. The method of claim 6, wherein said snares have more than one single strand capture DNA sequences on one single snare.

11. The method of claim 10, wherein the labels are different for different single strand capture DNA sequences on one single snare so that different DNA sequences can be detected on one single snare.

12. The method of claim 6, wherein said test column have an additional snare without capture DNA thereon.

13. The method of claim 6, wherein said enzyme is S1 nuclease.

14. A method for detecting the presence of a DNA sequence in a test sample comprises the steps of:

(a) providing a positive control single strand DNA sequence;

(b) denaturing a test sample to form a single strand target DNA sequence for which detection is being sought;

(c) adding the test sample and the positive control DNA sequence to a test column, wherein the column has at least two snares, said snares being separate spatially one from another by an intervening air space and not in contact with one another; one of said snares having thereon a first control single strand capture DNA sequence for binding to a portion of the positive control DNA sequence; at least one of said snares thereon having a target single strand capture DNA sequence specific to a corresponding target DNA sequence in the test sample, so that the positive control DNA sequence binds with the first control single strand capture DNA sequence wherein the bound positive control DNA sequence has a double strand portion and a single strand portion; and the target DNA sequence present in the test sample binds with the target capture DNA sequence wherein the bound target DNA sequence has a double strand portion and a single strand portion;

(d) adding a wash solution to the column to remove unbound DNA;

(e) adding DNA probes to provide detectable labels for attachment to the single strand portion of the bound positive control DNA sequence and the single strand portion of the bound target DNA sequence formed in step (c);

(f) adding a wash solution to the column to remove unbound DNA probes; and (g) detecting any signals each snare.

15. The method of claim 14, wherein the method further includes adding a substrate which reacts with the labels to give off detectable signals.

16. The method of claim 14, wherein the positive control single strand DNA sequence is prepared from a target DNA sequence for which detection is being sought, by a process selected from the group consisting of (1) inserting a control DNA fragment into the target DNA sequence at a predetermined scission point; and (2) removing a small fragment of DNA from the target DNA at a predetermined scission point.

17. The method of claim 14, wherein the positive control DNA is added into the test column in one way selected from the group consisting of (1) separately from the test sample, and (2) being added into said test sample prior to introducing the sample into the test column.

18. The method of claim 14, wherein step (c) further include adding a negative control DNA sequence to the test column; wherein the test column also has a control snare having thereon a second control single strand capture DNA sequence for binding to the negative control DNA sequence, so that the negative control DNA sequence binds with the second control capture sequence to form a bound negative control DNA sequence.

19. The method of claim 18, wherein the method further comprises preparation of a negative control single strand DNA sequence; wherein the negative control DNA sequence has a DNA sequence which is different from the target DNA sequence and different from the positive control DNA sequence.

20. The method of claim 14, wherein said test column have an additional snare without capture DNA thereon.

21. The method of claim 14, wherein said snares have more than one single strand capture DNA sequences on one single snare.

22. The method of claim 21, wherein the probes and the labels are different for different single strand DNA sequences bound on one single snare so that different DNA sequences can be detected on one single snare.

23. A method for detecting the presence of a RNA sequence in a test sample comprises the steps of:

(a) providing a positive control single strand DNA sequence;

(b) adding a test sample and the positive control DNA sequence to a test column wherein the column has at least two snares, one of said snares having thereon a first control single strand capture DNA sequence for binding to the positive control DNA sequence; at least one of said snares thereon having a target single strand capture DNA sequence specific to a corresponding target RNA sequence in the test sample, so that the positive control DNA sequence binds with the first control capture DNA sequence to form a double strand positive control DNA sequence, and the RNA sequence present in the test sample binds with the target capture DNA sequence to form a double strand DNA/RNA complex;

(c) adding a wash solution to the column to remove unbound positive control DNA and target RNA;

(d) adding an enzyme to the column to destroy single strand DNA and RNA;

(e) adding a denaturing solution to separate the formed double strand control DNA sequence and double strand DNA/RNA complex, then adding a wash solution to remove denatured non-capture DNA and RNA sequences, so that the single strand capture DNA sequences re-form on each snare;

(f) adding DNA probes to provide detectable labels for single strand capture DNA sequences formed in step (e);

(g) adding a wash solution to the column to remove unbound DNA probes; and (h) detecting any signals from each snare.

24. The method of claim 23, wherein the method further includes adding a substrate which reacts with the labels to give off detectable signals.

25. The method of claim 23, wherein the positive control DNA sequence is different from the target RNA sequence and the first control capture DNA sequence is different from the target capture DNA sequence; wherein the DNA probes used in step (f) are different for the first control capture sequence and the target capture sequence.

26. The method of claim 23, wherein the positive control DNA sequence has a portion which has the same sequence to a portion of the target RNA sequence; wherein the first control capture DNA and the target capture DNA have a common sequence at a portion of the capture sequences, so that a common DNA probe is used in step (f) for detection of the re-formed control and target capture sequences.

27. The method of claim 23, wherein step (a) further includes providing a negative control single strand DNA sequence which is different from the target RNA sequence and different from the positive control DNA sequence; wherein step (b) further includes adding the negative control DNA to the test column which also has a control snare having thereon a second control single strand capture DNA sequence; wherein the second control capture DNA sequence partially matches the negative control DNA sequence so that the negative control DNA sequence binds with the second control capture DNA sequence to form a double strand DNA sequence which also has unbound single strand portions; wherein in step (f) DNA probes do not match re-formed partial second control single strand capture DNA sequence formed in step (e), and no binding occurs between the probes and the second control capture, therefore, in step (h) no signal is detected from the second control snare under normal conditions.

28. The method of claim 27, wherein the second control capture DNA sequence is different from the target capture DNA and the first control capture DNA sequences.

29. The method of claim 27, wherein the first control capture DNA, the second control capture DNA and the target capture DNA have a common sequence at a portion of the capture sequences; and a common DNA probe is used in step (f) for detection of the re-formed control and target capture sequences.

30. The method of claim 27, wherein control DNA sequences are added into the test column in one way selected from the group consisting of (1) separately from the test sample, and (2) being added into said test sample prior to introducing the sample into the test column.

31. The method of claim 23, wherein said snares have more than one single strand capture DNA sequences on one single snare.

32. The method of claim 31, wherein the labels are different for different capture DNA sequences on one single snare so that different DNA sequences can be detected on one single snare.

33. The method of claim 23, wherein said test column have an additional snare without capture DNA thereon.

34. The method of claim 23, wherein said enzyme is S1 nuclease.

35. A column for detection of a test material, wherein the column has at least two snares, one of said snares having thereon a first control capture material for detecting the presence of a first control material, and at least one of said snares having thereon a test capture material for detecting a test material for which detection is being sought, and wherein said snares are separate spatially one from another by an intervening air space so that said snares are not in contact with one another.

36. The column of claim 35, wherein the column has a snare having thereon a first control capture material, and a plurality of snares each having thereon a specific test capture material for detecting a specific test material for which detection is being sought; wherein the test capture materials are different from one another.

37. The column of claim 35, wherein the column has a snare having thereon a first control capture material, at least one snare having thereon a test capture material for detecting a test material for which detection is being sought, and a snare having thereon a second control capture material for detecting the presence of a second control material.

38. The column of claim 35, wherein the snares are separated longitudinally along the column.

39. The column of claim 35, wherein the column comprises at least two chambers, each chamber having a snare, one of said chambers having a first control capture material on the snare for detecting the presence of a first control material, and at least one of said chambers having a test capture material on the snare for detecting the test material for which detection is being sought.

40. The column of claim 39, wherein the column further has a chamber having a second control material on the snare for detecting the presence of a second control material.

41. The column of claim 39, wherein said chambers have a connecting means to connect different chambers in order, and the chambers are connected along the longitudinal axis of the chamber through the connecting means.

42. A kit which comprises (a) a column for analysis of a test material, wherein said column has at least two snares, one of said snares having thereon a first control capture material for detecting the presence of a first control material, and at least one of said snares having thereon a target capture material for detecting a test material for which detection is being sought, and wherein said snares are separate spatially one from another by an intervening air space so that said snares are not in contact with one another; and (b) reagents for detecting the presence of the test materials.

43. The kit of claim 42, wherein said snare is contained in a chamber; wherein at least two chambers are connected together to form said column.

* * * * *